(12) United States Patent
Chen et al.

(10) Patent No.: US 6,849,426 B2
(45) Date of Patent: Feb. 1, 2005

(54) METHODS AND REAGENTS FOR DETECTING ENDOTOXIN

(75) Inventors: Lin Chen, Frederick, MD (US); Michael Pepe, Frederick, MD (US)

(73) Assignee: Cambrex Bio Science Walkersville, Inc., Walkersville, MD (US)

(*) Notice: Subject to any disclaimer, the term of this patent is extended or adjusted under 35 U.S.C. 154(b) by 72 days.

(21) Appl. No.: 10/183,992

(22) Filed: Jun. 28, 2002

(65) Prior Publication Data

US 2003/0054432 A1 Mar. 20, 2003

Related U.S. Application Data

(60) Provisional application No. 60/310,125, filed on Jun. 28, 2001.

(51) Int. Cl.[7] .............................................. C12P 21/06
(52) U.S. Cl. ..................................................... 435/69.1
(58) Field of Search ........................ 435/69.1; 530/350; 514/2

(56) References Cited

U.S. PATENT DOCUMENTS

| | | | |
|---|---|---|---|
| 4,322,217 A | * | 3/1982 | Dikeman .................... 435/7.21 |
| 5,389,547 A | * | 2/1995 | Tanaka et al. ................. 436/94 |
| 5,712,144 A | | 1/1998 | Ding et al. |
| 5,716,834 A | | 2/1998 | Ding et al. |
| 5,760,177 A | | 6/1998 | Iwanaga et al. |
| 5,858,706 A | | 1/1999 | Ding et al. |
| 5,985,590 A | | 11/1999 | Ding et al. |
| 6,168,924 B1 | * | 1/2001 | Tamura et al. ............... 435/7.1 |

OTHER PUBLICATIONS

Nakamura et al., "Intracellular serine-protease zymogen, factor C, from horseshoe crab hemocytes. Its activation by synthetic lipid A analogues and acidic phospholipids", Eur. J. Biochem., 1988, pp 89–94, vol. 176(1).

Tan et al., "High–affinity LPS binding domain(s) in recombinant factor C of a horseshoe crab neutralizes LPS–Induced lethality", The FASEB Journal, May 2000, 859–870, vol. 14.

Tokunaga et al, "Further Studies on Lipopolysaccharide–Sensitive Serine Protease Zymogen (Factor C): Its Isolation from Limulus polyphemus Hemocytes and Identification as an Intracellular Zymogen Activated by α–Chymotrypsin, Not by Trypsin", J. Biochem., 1991, pp 150–157, vol. 109.

Muta et al., "Limulus factor C. An endotoxin–sensitive serine protease zymogen with a mosaic structure of complement–like, epidermal growth factor–like, and lectin–like domains", Journal of Biological Chemistry, Apr. 5, 1991, vol. 266, No. 10, pp. 6554–6561.

* cited by examiner

Primary Examiner—Karen Cochrane Carlson
Assistant Examiner—Sheridan Snedden
(74) Attorney, Agent, or Firm—Banner & Witcoff, Ltd.

(57) ABSTRACT

A reagent containing a purified horseshoe crab Factor C, particularly a recombinantly produced Factor C, and a surfactant can be used in a sensitive, rapid, and reproducible assay to detect endotoxin.

44 Claims, 11 Drawing Sheets

SEQUENCE LISTING

<160> NUMBER OF SEQ ID NOS: 8

<210> SEQ ID NO 1
<211> LENGTH: 1906
<212> TYPE: DNA
<213> ORGANISM: Tachypleudus tridentata

<400> SEQUENCE: 1

```
gtaagtatca tcaggtttaa cgcgaacgtg gaagaactct gaaggtaact taagtatggt      60
cttagcgtcg tttttggtgt ctggtttagt tctagggata ctagcccaac aaatgcgtcc     120
agttcagtcc agaggagtag atctgggctt gtgtgatgaa acgaggttcg agtgtaagtg     180
tggagatcca ggctatgtgt tcaacgtccc tatgaaacaa tgcacgtact tctatcgatg     240
gaggccttat tgtaaaccat gtgatgacct ggaggctaag gacatttgtc caaagtacaa     300
acgatgtcaa gagtgtaagg ctggtcttga tagttgtgtt acttgtccac ctaacaaata     360
tggtacttgg tgtagcggtg aatgtcaatg taagaatgga ggtatctgtg accagaggac     420
aggagcttgt acctgtcgtg acagatatga aggagcgcac tgtgaaattc tcaaaggttg     480
tcctcttctt ccatcggatt ctcaagttca ggaagtcaga aacccaccag ataatcccca     540
aactattgac tacagctgtt caccagggtt caagcttaaa ggcgtggcac gaattagctg     600
tctcccaaat ggacagtgga gtagctttcc acccaaatgt attcgagaat gtgccaaggt     660
ttcatctcca gaacacggga aagtgaatgc tcctagtggc aatatgatag aagggctac      720 tttacggttc tcatgtgata gtccctacta cttgattggt caagaaacat taacctgcca     780
gggtaatggt cagtggagtg gacaaatacc acaatgtaag aagttggtct tctgtcctga     840
ccttgatcct gtaaaccatg ctgaacacca ggttaaaatt ggtgtggaac aaaaatatgg     900
tcagtttcct caaggcactg aagtgaccta tacgtgttcg ggtaactact tcttgatggg     960 tttttaacacc ttaaaatgta accctgatgg gtcctggtca ggatcacagc catcctgtgt    1020
taaagtggca gacagagagg tcgactgtga cagtaaagct gtagacttct tggatgatgt    1080 tgtgaacct gtcaggatcc actgtcctgc tggctgttct ttgacagctg gtactgtgtg     1140
gggtacagcc atataccacg aactttcctc agtgtgtcgt gcagccatcc atgctggcaa    1200
gcttccaaac tctggagggg cggtgcatgt agtgaacaat ggcccctact cggactttct    1260
```

-continued

```
gggtagtgac ctgaatggga taaaatcgga agagttgaag tctcttgccc gcagttttcg      1320
atttgattat gtcagttcat ccacagcagg tagatcagga tgtcctgatg gatggtttga      1380
ggtagaagag aactgtgtgt acgttacatc aaaacagaga gcctgggaaa gagctcaagg      1440
tgtgtgtacc aatatggctg ctcgtcttgc tgtgctagac aaagatctaa ttccgagttc      1500
cttgactgag actctacgag ggaaaggtac tgataatgtt actgcaacct aagtagactt      1560
tattttagtc taagatatct tgtgtcaatt gttgacttgc tactcttact ttattgtaat      1620
aaaactgtta taaagtatta agtcttgttt attttattac tgtttaaagt atactacaag      1680
ggttacacct aaaaggaaat tctatctga caatttcata aaaagtggat gttacttttg       1740
attttcgttg gttgttaaat gcacatccgg tttgtaaaca tctaagttcc cacaaacagg      1800
ctctgtggtc ttgtaaaaat ctaaactaat accacttta atatgttta aacctttttt        1860 ttatgtatgc ttatcagaga ctaaaataaa ggttttaat aactgt                      1906
```

<210> SEQ ID NO 2
<211> LENGTH: 498
<212> TYPE: PRT
<213> ORGANISM: Tachypleudus tridentata

<400> SEQUENCE: 2

```
Met Val Leu Ala Ser Phe Leu Val Ser Gly Leu Val Leu Gly Ile Leu
  1               5                  10                  15

Ala Gln Gln Met Arg Pro Val Gln Ser Arg Gly Val Asp Leu Gly Leu
             20                  25                  30

Cys Asp Glu Thr Arg Phe Glu Cys Lys Cys Gly Asp Pro Gly Tyr Val
         35                  40                  45

Phe Asn Val Pro Met Lys Gln Cys Thr Tyr Phe Tyr Arg Trp Arg Pro
     50                  55                  60

Tyr Cys Lys Pro Cys Asp Asp Leu Glu Ala Lys Asp Ile Cys Pro Lys
 65                  70                  75                  80

Tyr Lys Arg Cys Gln Glu Cys Lys Ala Gly Leu Asp Ser Cys Val Thr
                 85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Thr Cys Arg
        115                 120                 125

Asp Arg Tyr Glu Gly Ala His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Val Ala Arg Ile Ser Cys Leu Pro Asn Gly Gln Trp Ser Ser Phe Pro
            180                 185                 190

Pro Lys Cys Ile Arg Glu Cys Ala Lys Val Ser Ser Pro Glu His Gly
        195                 200                 205

Lys Val Asn Ala Pro Ser Gly Asn Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Ser Gly Gln Ile Pro Gln Cys Lys Lys
                245                 250                 255
```

-continued

```
Leu Val Phe Cys Pro Asp Leu Asp Pro Val Asn His Ala Glu His Gln
            260                 265                 270

Val Lys Ile Gly Val Glu Gln Lys Tyr Gly Gln Phe Pro Gln Gly Thr
        275                 280                 285

Glu Val Thr Tyr Thr Cys Ser Gly Asn Tyr Phe Leu Met Gly Phe Asn
    290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
        355                 360                 365

Glu Leu Ser Ser Val Cys Arg Ala Ala Ile His Ala Gly Lys Leu Pro
    370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Glu Leu Lys Ser
                405                 410                 415

Leu Ala Arg Ser Phe Arg Phe Asp Tyr Val Ser Ser Thr Ala Gly
            420                 425                 430

Arg Ser Gly Cys Pro Asp Gly Trp Phe Glu Val Glu Glu Asn Cys Val
        435                 440                 445

Tyr Val Thr Ser Lys Gln Arg Ala Trp Glu Arg Ala Gln Gly Val Cys
    450                 455                 460

Thr Asn Met Ala Ala Arg Leu Ala Val Leu Asp Lys Asp Leu Ile Pro
465                 470                 475                 480

Ser Ser Leu Thr Glu Thr Leu Arg Gly Lys Gly Thr Asp Asn Val Thr
                485                 490                 495

Ala Thr

<210> SEQ ID NO 3
<211> LENGTH: 3467
<212> TYPE: DNA
<213> ORGANISM: Tachypleudus tridentata

<400> SEQUENCE: 3
caggtttaac gcgaacgtgg aagaactctg aaggtaactt aagtatggtc ttagcgtcgt    60
ttttggtgtc tggtttagtt ctagggatac tagcccaaca aatgcgtcca gttcagtcca   120
gaggagtaga tctgggcttg tgtgatgaaa cgaggttcga gtgtaagtgt ggagatccag   180
gctatgtgtt caacgtccct atgaaacaat gcacgtactt ctatcgatgg aggccttatt   240
gtaaaccatg tgatgacctg gaggctaagg acatttgtcc aaagtacaaa cgatgtcaag   300
agtgtaaggc tggtcttgat agttgtgtta cttgtccacc taacaaatat ggtacttggt   360
gtagcggtga atgtcaatgt aagaatggag gtatctgtga ccagaggaca ggagcttgta   420
cctgtcgtga cagatatgaa ggagcgcact gtgaaattct caaggttgt cctcttcttc   480
catcggattc tcaagttcag gaagtcagaa acccaccaga taatcccaa actattgact   540
acagctgttc accagggttc aagcttaaag gcgtggcacg aattagctgt ctcccaaatg   600
gacagtggag tagcttttcca cccaaatgta ttcgagaatg tgccaaggtt tcatctccag   660
aacacgggaa agtgaatgct cctagtggca atatgataga agggctact ttacggttct   720
```

-continued

```
catgtgatag tccctactac ttgattggtc aagaaacatt aacctgccag ggtaatggtc     780
agtggagtgg acaaatacca caatgtaaga agttggtctt ctgtcctgac cttgatcctg     840
taaaccatgc tgaacaccag gttaaaattg gtgtggaaca aaaatatggt cagtttcctc     900
aaggcactga agtgacctat acgtgttcgg gtaactactt cttgatgggt tttaacacct     960
taaaatgtaa ccctgatggg tcctggtcag gatcacagcc atcctgtgtt aaagtggcag    1020
acagagaggt cgactgtgac agtaaagctg tagacttctt ggatgatgtt ggtgaacctg    1080
tcaggatcca ctgtcctgct ggctgttctt tgacagctgg tactgtgtgg gtacagccag    1140
tataccacga actttcctca gtgtgtcgtg cagccatcca tgctggcaag cttccaaact    1200
ctggaggggc ggtgcatgta gtgaacaatg gccccctactc ggactttctg ggtagtgacc    1260
tgaatgggat aaaatcggaa gagttgaagt ctcttgcccg cagttttcga tttgattatg    1320
tcagttcatc cacagcaggt agatcaggat gtcctgatgg atggtttgag gtagaagaga    1380
actgtgtgta cgttacatca aaacagagag cctgggaaag agctcaaggt gtgtgtacca    1440
atatggctgc tcgtcttgct gtgctagaca aagatctaat tccgagttcc ttgactgaga    1500
ctctacgagg gaaagggtta acaaccacat ggataggatt gcacagacta gatgctgaga    1560
agcccttttgt ttgggagcta atggatcgta gtaatgtggt tctgaatgat aacctaacat    1620
tctgggcctc tggcgaacct ggaaatgaaa ctaactgtgt atatctggac atccgagatc    1680
agctgcagcc tgtgtggaaa accaagtcat gttttcagcc ctcaagcttt gcttgcatga    1740
tggatttgtc agacagaaat aaagccaaat gcgatgaccc tggaccactg aaaatggac    1800
acgccacact tcatggacaa agtattgatg ggttctatgc tggttcttct ataaggtaca    1860
gctgtgaggt tctccactac ctcagtggaa ctgagaccgt aacttgtaca acaaatggca    1920
catggagtgc tcctaaacct cgatgtatca agtcatcac ctgccaaaac cctcctgtac    1980
catcatatgg ttctgtggaa atcaaacccc caagtcggac aaaactcgatc agtcgtgttg    2040
ggtcaccttt cttgaggttg ccacggttac ccctcccatt agccagagca gccaaacctc    2100
ctccaaaacc tagatcctca caaccctcta ctgtggactt ggcttctaaa gttaaactac    2160
ctgaaggtca ttaccgggta gggtctcgag ccatttacac gtgcgagtcg agatactacg    2220
aactacttgg atctcaaggc agaagatgtg actctaatgg aaactggagt ggtcggcccg    2280
ctagctgtat tccagtttgt ggacggtcag actctcctcg ttctccttc atctggaatg    2340
ggaattctac agaaataggt cagtggccgt ggcaggcagg aatctctcga tggcttgcag    2400
accacaatat gtggtttctc cagtgtggag gatccctatt gaatgagaaa tggatcgtca    2460
ctgctgccca ctgtgtcacc tactctgcta ctgctgagat aattgatccc agtcagttta    2520
aaatctatct gggcaagtac taccgtgatg acagtagaga cgatgactac gtacaagtaa    2580
gagaggctct cgagatccac gtaaatccta actacgaccc cggcaatctc aactttgaca    2640
tagccctaat tcaactgaaa actcctgtta ctttgacaac acgagtccaa ccaatctgtc    2700
tgcctactga catcacaaca agagaacact tgaaggaggg aacattagca gtggtgacag    2760
gttgggggttt gaatgaaaac aacacatatt cagagatgat tcaacaagct gtgctacctg    2820
ttgttgcagc aagcacctgt gaagaggggt acaaggaagc agacttacca ctgacagtaa    2880
cagagaacat gttctgtgca ggttacaaga agggacgtta tgatgcctgc agtgggggaca    2940
gtggaggacc attagtgttt gctgatgatt cccgtaccga aaggcggtgg gtcttggaag    3000
ggattgtcag ctggggcagt cccagtggat gtggcaaggc taaccagtat ggggggcttca    3060
ctaaagttaa cgttttttcta tcatggatta ggcagttcat ttgaaactga tctaaatatt    3120
```

-continued

```
ttaatcatgg ttataaacgt cttgtttcct attttttgctt tactagttta acccataaga    3180
aggttaagtg ggtaaggcac cagtgtcatt gtttgtttgt ttttacaaat ggttcgttta    3240
gtcaatgaat gagaatagta tccattggac actgttacct tttatgtttt tattctacct    3300 tttatatta ccatgcaagt atttggaata tcttctatac atatgaaaat tctgttattt    3360
ttccataaag ttggtttctg gtgtgcgtta agtccaccac tggagaatga tgtaattttc    3420
actagtacat gaaataaata tagaacaaat ctattataaa ctacctt                   3467
```

<210> SEQ ID NO 4
<211> LENGTH: 1019
<212> TYPE: PRT
<213> ORGANISM: Tachypleudus tridentata

<400> SEQUENCE: 4

```
Met Val Leu Ala Ser Phe Leu Val Ser Gly Leu Val Leu Gly Ile Leu
 1               5                  10                  15

Ala Gln Gln Met Arg Pro Val Gln Ser Arg Gly Val Asp Leu Gly Leu
             20                  25                  30

Cys Asp Glu Thr Arg Phe Glu Cys Lys Cys Gly Asp Pro Gly Tyr Val
         35                  40                  45

Phe Asn Val Pro Met Lys Gln Cys Thr Tyr Phe Tyr Arg Trp Arg Pro
     50                  55                  60

Tyr Cys Lys Pro Cys Asp Asp Leu Glu Ala Lys Asp Ile Cys Pro Lys
 65                  70                  75                  80

Tyr Lys Arg Cys Gln Glu Cys Lys Ala Gly Leu Asp Ser Cys Val Thr
                 85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Thr Cys Arg
        115                 120                 125

Asp Arg Tyr Glu Gly Ala His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Val Ala Arg Ile Ser Cys Leu Pro Asn Gly Gln Trp Ser Ser Phe Pro
            180                 185                 190

Pro Lys Cys Ile Arg Glu Cys Ala Lys Val Ser Ser Pro Glu His Gly
        195                 200                 205

Lys Val Asn Ala Pro Ser Gly Asn Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Ser Gly Gln Ile Pro Gln Cys Lys Lys
                245                 250                 255

Leu Val Phe Cys Pro Asp Leu Asp Pro Val Asn His Ala Glu His Gln
            260                 265                 270

Val Lys Ile Gly Val Glu Gln Lys Tyr Gly Gln Phe Pro Gln Gly Thr
        275                 280                 285

Glu Val Thr Tyr Thr Cys Ser Gly Asn Tyr Phe Leu Met Gly Phe Asn
    290                 295                 300

Thr Leu Lys Cys Asn Pro Asp Gly Ser Trp Ser Gly Ser Gln Pro Ser
```

-continued

```
         305                 310                 315                 320
Cys Val Lys Val Ala Asp Arg Glu Val Asp Cys Asp Ser Lys Ala Val
                 325                 330                 335
Asp Phe Leu Asp Asp Val Gly Glu Pro Val Arg Ile His Cys Pro Ala
                 340                 345                 350
Gly Cys Ser Leu Thr Ala Gly Thr Val Trp Gly Thr Ala Ile Tyr His
                 355                 360                 365
Glu Leu Ser Ser Val Cys Arg Ala Ala Ile His Ala Gly Lys Leu Pro
    370                 375                 380
Asn Ser Gly Gly Ala Val His Val Asn Asn Gly Pro Tyr Ser Asp
385                 390                 395                 400
Phe Leu Gly Ser Asp Leu Asn Gly Ile Lys Ser Glu Glu Leu Lys Ser
                 405                 410                 415
Leu Ala Arg Ser Phe Arg Phe Asp Tyr Val Ser Ser Thr Ala Gly
                 420                 425                 430
Arg Ser Gly Cys Pro Asp Gly Trp Phe Glu Val Glu Asn Cys Val
    435                 440                 445
Tyr Val Thr Ser Lys Gln Arg Ala Trp Glu Arg Ala Gln Gly Val Cys
    450                 455                 460
Thr Asn Met Ala Ala Arg Leu Ala Val Leu Asp Lys Asp Leu Ile Pro
465                 470                 475                 480
Ser Ser Leu Thr Glu Thr Leu Arg Gly Lys Gly Leu Thr Thr Thr Trp
                 485                 490                 495
Ile Gly Leu His Arg Leu Asp Ala Glu Lys Pro Phe Val Trp Glu Leu
                 500                 505                 510
Met Asp Arg Ser Asn Val Val Leu Asn Asp Asn Leu Thr Phe Trp Ala
                 515                 520                 525
Ser Gly Glu Pro Gly Asn Glu Thr Asn Cys Val Tyr Leu Asp Ile Arg
    530                 535                 540
Asp Gln Leu Gln Pro Val Trp Lys Thr Lys Ser Cys Phe Gln Pro Ser
545                 550                 555                 560
Ser Phe Ala Cys Met Met Asp Leu Ser Asp Arg Asn Lys Ala Lys Cys
                 565                 570                 575
Asp Asp Pro Gly Pro Leu Glu Asn Gly His Ala Thr Leu His Gly Gln
                 580                 585                 590
Ser Ile Asp Gly Phe Tyr Ala Gly Ser Ser Ile Arg Tyr Ser Cys Glu
    595                 600                 605
Val Leu His Tyr Leu Ser Gly Thr Glu Thr Val Thr Cys Thr Thr Asn
    610                 615                 620
Gly Thr Trp Ser Ala Pro Lys Pro Arg Cys Ile Lys Val Ile Thr Cys
625                 630                 635                 640
Gln Asn Pro Pro Val Pro Ser Tyr Gly Ser Val Glu Ile Lys Pro Pro
                 645                 650                 655
Ser Arg Thr Asn Ser Ile Ser Arg Val Gly Ser Pro Phe Leu Arg Leu
                 660                 665                 670
Pro Arg Leu Pro Leu Pro Leu Ala Arg Ala Ala Lys Pro Pro Lys
                 675                 680                 685
Pro Arg Ser Ser Gln Pro Ser Thr Val Asp Leu Ala Ser Lys Val Lys
    690                 695                 700
Leu Pro Glu Gly His Tyr Arg Val Gly Ser Arg Ala Ile Tyr Thr Cys
705                 710                 715                 720
Glu Ser Arg Tyr Tyr Glu Leu Leu Gly Ser Gln Gly Arg Arg Cys Asp
                 725                 730                 735
```

-continued

Ser Asn Gly Asn Trp Ser Gly Arg Pro Ala Ser Cys Ile Pro Val Cys
        740                 745                 750

Gly Arg Ser Asp Ser Pro Arg Ser Pro Phe Ile Trp Asn Gly Asn Ser
        755                 760                 765

Thr Glu Ile Gly Gln Trp Pro Trp Gln Ala Gly Ile Ser Arg Trp Leu
        770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Ser Gln Phe Lys Ile Tyr Leu Gly Lys Tyr
        820                 825                 830

Tyr Arg Asp Asp Ser Arg Asp Asp Tyr Val Gln Val Arg Glu Ala
        835                 840                 845

Leu Glu Ile His Val Asn Pro Asn Tyr Asp Pro Gly Asn Leu Asn Phe
850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Thr Arg Glu His Leu
                885                 890                 895

Lys Glu Gly Thr Leu Ala Val Val Thr Gly Trp Gly Leu Asn Glu Asn
        900                 905                 910

Asn Thr Tyr Ser Glu Met Ile Gln Gln Ala Val Leu Pro Val Val Ala
        915                 920                 925

Ala Ser Thr Cys Glu Glu Gly Tyr Lys Glu Ala Asp Leu Pro Leu Thr
        930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975

Arg Thr Glu Arg Arg Trp Val Leu Glu Gly Ile Val Ser Trp Gly Ser
        980                 985                 990

Pro Ser Gly Cys Gly Lys Ala Asn Gln Tyr Gly Gly Phe Thr Lys Val
        995                 1000                1005

Asn Val Phe Leu Ser Trp Ile Arg Gln Phe Ile
        1010                1015

<210> SEQ ID NO 5
<211> LENGTH: 4182
<212> TYPE: DNA
<213> ORGANISM: Carcinoscorpius rotundicauda

<400> SEQUENCE: 5
gtatttaatg tctcaacggt aaaggtttca ttgtagctaa tatttaactt cctccctgtg      60
ccccaaatcg cgagtatgac gtcagttaag acttcgtatt ttaagagtta aacacgagcc     120
ttaaagagcg atatttttt tgttaaacac ttccaactta atacaattgg caaactttca     180
aaaataaagt ggaaaggag gtaaaaaga tgaaaaaaat tcgcatacaa tagaatacaa      240
taaaatgtgt tgtctttact gtcaacactt actgttcgtt cggtcacagc tgtgaatcgg     300
ggtgacttta tgtttgtagt ggtcttaaaa acgggtactt ggttgttttg aaaattttaa     360
aacctacata tgattctcct aaaattttgt ttataaatta gcaccatttg cgacctaaat     420
cttttttgta gtcttaagtt tagttgacat aaaaacaaaa tttgtaacaa cacacggtat     480

```
aaactaaata gcttcagatg ggtcgtatga caaggaaact tttaaataat tatgaaagtt      540
tttttaaaat ttgactaagg tttagattat gtgggtgaca tgcttcgaca cgtttcttt       600 tgtttgtgaa agttcagttt tctgtttgtt gtgtgtgtgg aggtttggtt tctgtaggtg      660
gcgtgttttc tacagttttc cattcgttaa gtcaacagtt gttttattac agtgttacca      720
ttactctctc cacaatacct caaagttcta ctctgtgaat cctgacaagc cagagtacat      780
tctttcaggt ttagttctag ggctactagc ccaaaaaatg cgcccagttc agtccaaagg      840
agtagatcta ggcttgtgtg atgaaacgag gttcgagtgt aagtgtggcg atccaggcta      900
tgtgttcaac attccagtga aacaatgtac atacttttat cgatggaggc cgtattgtaa      960
accatgtgat gacctggagg ctaaggatat ttgtccaaag tacaaacgat gtcaagagtg     1020
taaggctggt cttgatagtt gtgttacttg tccacctaac aaatatggta cttggtgtag     1080
cggtgaatgt cagtgtaaga atggaggtat ctgtgaccag aggacaggag cttgtgcatg     1140
tcgtgacaga tatgaagggg tgcactgtga aattctcaaa ggttgtcctc ttcttccatc     1200
ggattctcag gttcaggaag tcagaaatcc accagataat ccccaaacta ttgactacag     1260
ctgttcacca gggttcaagc ttaagggtat ggcacgaatt agctgtctcc caaatggaca     1320
gtggagtaac tttccaccca atgtattcg agaatgtgcc atggtttcat ctccagaaca     1380
tgggaaagtg aatgctctta gtggtgatat gatagaaggg gctactttac ggttctcatg     1440
tgatagtccc tactacttga ttggtcaaga acattaacc tgtcagggta atggtcagtg      1500
gaatggacag ataccacaat gtaagaactt agtcttctgt cctgacctgg atcctgtaaa     1560
ccatgctgaa cacaaggtta aaattggtgt ggaacaaaaa tatggtcagt tccctcaagg     1620
cactgaagtg acctatacgt gttcgggtaa ctacttcttg atgggttttg acaccttaaa     1680
atgtaaccct gatgggtctt ggtcaggatc acagccatcc tgtgttaaag tggcagacag     1740
agaggtcgac tgtgacagta aagctgtaga cttcttggat gatgttggtg aacctgtcag     1800
gatccactgt cctgctggct gttctttgac agctggtact gtgtggggta cagccatata     1860
ccatgaactt tcctcagtgt gtcgtgcagc catccatgct ggcaagcttc caaactctgg     1920
aggagcggtg catgttgtga caatggccc ctactcggac tttctgggta gtgacctgaa     1980
tgggataaaa tccgaagagt tgaagtctct tgcccggagt ttccgattcg attatgtcag     2040
ttcctccaca gcaggtaaat caggatgtcc tgatggatgg tttgaggtag acgagaactg     2100
tgtgtacgtt acatcaaaac agagagcctg ggaaagagct caaggtgtgt gtaccaatat     2160
ggctgctcgt cttgctgtgc tggacaaaga tgtaattcca aattcattga ctgagactct     2220
acgagggaaa gggttaacaa ccacgtggat aggattgcac agactagatg ctgagaagcc     2280
ctttatttgg gagttaatgg atcgtagtaa tgtggttctg aatgataacc taacattctg     2340
ggcctctggc gaacctggaa atgaaactaa ctgtgtatat atggacatcc aagatcagtt     2400
gcagtctgtg tggaaaacca agtcatgttt tcagccctca agttttgctt gcatgatgga     2460
tctgtcagac agaaataaag ccaaatgcga tgatcctgga tcactggaaa atggacacgc     2520
cacacttcat ggacaaagta ttgatgggtt ctatgctggt tcttctataa ggtacagctg     2580
tgaggttctc cactacctca gtggaactga aaccgtaact tgtacaacaa atggcacatg     2640
gagtgctcct aaacctcgat gtatcaaagt catcacctgc caaaaccccc ctgtaccatc     2700
atatggttct gtggaaatca aaccccaag tcggacaaac tcgataagtc gtgttgggtc     2760 accttcttg aggttgccac ggttacccct cccattagcc agagcagcca aacctcctcc     2820
aaaacctaga tcctcacaac cctctactgt ggacttggct tctaaagtta aactacctga     2880
```

-continued

```
aggtcattac cgggtagggt ctcgagccat ttacacgtgc gagtcgagat actacgaact    2940
acttggatct caaggcagaa gatgtgactc taatggaaac tggagtggtc ggccagcgag    3000
ctgtattcca gtttgtggac ggtcagactc tcctcgttct ccttttatct ggaatgggaa    3060
ttctacagaa ataggtcagt ggccgtggca ggcaggaatc tctagatggc ttgcagacca    3120
caatatgtgg tttctccagt gtggaggatc tctattgaat gagaaatgga tcgtcactgc    3180
tgcccactgt gtcacctact ctgctactgc tgagattatt gaccccaatc agtttaaaat    3240
gtatctgggc aagtactacc gtgatgacag tagagacgat gactatgtac aagtaagaga    3300
ggctcttgag atccacgtga atcctaacta cgaccccggc aatctcaact tgacatagc     3360 cctaattcaa ctgaaaactc ctgttacttt gacaacacga gtccaaccaa tctgtctgcc    3420
tactgacatc acaacaagag aacacttgaa ggagggaaca ttagcagtgg tgacaggttg    3480
gggtttgaat gaaaacaaca cctattcaga gacgattcaa caagctgtgc tacctgttgt    3540
tgcagccagc acctgtgaag agggtacaa ggaagcagac ttaccactga cagtaacaga     3600
gaacatgttc tgtgcaggtt acaagaaggg acgttatgat gcctgcagtg gggacagtgg    3660
aggaccttta gtgtttgctg atgattcccg taccgaaagg cggtgggtct tggaagggat    3720
tgtcagctgg ggcagtccca gtggatgtgg caaggcgaac cagtacgggg gcttcactaa    3780
agttaacgtt ttcctgtcat ggattaggca gttcatttga aactgatcta aatattttaa    3840
gcatggttat aaacgtcttg ttcctattat tgctttactg gtttaaccca taagaaggtt    3900 aacgggtaa ggcacaagga tcattgtttc tgtttgtttt tacaaatggt tcttttagtc     3960
agtgaatgag aatagtatcc attggagact gttacctttt attctacctt tttatattac    4020
tatgcaagta tttgggatat cttctacaca tgaaaattct gtcattttac cataaatttg    4080
gtttctggtg tgtgtgttaa gtccaccact agagaacgat gtaattttca atagtacatg    4140
aaataaatat agaacaaatc tattataaaa aaaaaaaaa aa                        4182
```

<210> SEQ ID NO 6
<211> LENGTH: 1083
<212> TYPE: PRT
<213> ORGANISM: Carcinoscorpius rotundicauda

<400> SEQUENCE: 6

```
Met Trp Val Thr Cys Phe Asp Thr Phe Leu Phe Val Cys Glu Ser Ser
  1               5                  10                  15

Val Phe Cys Leu Leu Cys Val Trp Arg Phe Gly Phe Cys Arg Trp Arg
             20                  25                  30

Val Phe Tyr Ser Phe Pro Phe Val Lys Ser Thr Val Val Leu Leu Gln
         35                  40                  45

Cys Tyr His Tyr Ser Leu His Asn Thr Ser Lys Phe Tyr Ser Val Asn
     50                  55                  60

Pro Asp Lys Pro Glu Tyr Ile Leu Ser Gly Leu Val Leu Gly Leu Leu
 65                  70                  75                  80

Ala Gln Lys Met Arg Pro Val Gln Ser Lys Gly Val Asp Leu Gly Leu
                 85                  90                  95

Cys Asp Glu Thr Arg Phe Glu Cys Lys Cys Gly Asp Pro Gly Tyr Val
            100                 105                 110

Phe Asn Ile Pro Val Lys Gln Cys Thr Tyr Phe Tyr Arg Trp Arg Pro
        115                 120                 125

Tyr Cys Lys Pro Cys Asp Asp Leu Glu Ala Lys Asp Ile Cys Pro Lys
    130                 135                 140
```

```
Tyr Lys Arg Cys Gln Glu Cys Lys Ala Gly Leu Asp Ser Cys Val Thr
145                 150                 155                 160

Cys Pro Pro Asn Lys Tyr Gly Thr Trp Cys Ser Gly Glu Cys Gln Cys
                165                 170                 175

Lys Asn Gly Gly Ile Cys Asp Gln Arg Thr Gly Ala Cys Ala Cys Arg
            180                 185                 190

Asp Arg Tyr Glu Gly Val His Cys Glu Ile Leu Lys Gly Cys Pro Leu
        195                 200                 205

Leu Pro Ser Asp Ser Gln Val Gln Glu Val Arg Asn Pro Pro Asp Asn
    210                 215                 220

Pro Gln Thr Ile Asp Tyr Ser Cys Ser Pro Gly Phe Lys Leu Lys Gly
225                 230                 235                 240

Met Ala Arg Ile Ser Cys Leu Pro Asn Gly Gln Trp Ser Asn Phe Pro
                245                 250                 255

Pro Lys Cys Ile Arg Glu Cys Ala Met Val Ser Ser Pro Glu His Gly
                260                 265                 270

Lys Val Asn Ala Leu Ser Gly Asp Met Ile Glu Gly Ala Thr Leu Arg
            275                 280                 285

Phe Ser Cys Asp Ser Pro Tyr Tyr Leu Ile Gly Gln Glu Thr Leu Thr
        290                 295                 300

Cys Gln Gly Asn Gly Gln Trp Asn Gly Gln Ile Pro Gln Cys Lys Asn
305                 310                 315                 320

Leu Val Phe Cys Pro Asp Leu Asp Pro Val Asn His Ala Glu His Lys
                325                 330                 335

Val Lys Ile Gly Val Glu Gln Lys Tyr Gly Gln Phe Pro Gln Gly Thr
            340                 345                 350

Glu Val Thr Tyr Thr Cys Ser Gly Asn Tyr Phe Leu Met Gly Phe Asp
        355                 360                 365

Thr Leu Lys Cys Asn Pro Asp Gly Ser Trp Ser Gly Ser Gln Pro Ser
    370                 375                 380

Cys Val Lys Val Ala Asp Arg Glu Val Asp Cys Asp Ser Lys Ala Val
385                 390                 395                 400

Asp Phe Leu Asp Asp Val Gly Glu Pro Val Arg Ile His Cys Pro Ala
                405                 410                 415

Gly Cys Ser Leu Thr Ala Gly Thr Val Trp Gly Thr Ala Ile Tyr His
                420                 425                 430

Glu Leu Ser Ser Val Cys Arg Ala Ala Ile His Ala Gly Lys Leu Pro
            435                 440                 445

Asn Ser Gly Gly Ala Val His Val Val Asn Asn Gly Pro Tyr Ser Asp
    450                 455                 460

Phe Leu Gly Ser Asp Leu Asn Gly Ile Lys Ser Glu Glu Leu Lys Ser
465                 470                 475                 480

Leu Ala Arg Ser Phe Arg Phe Asp Tyr Val Ser Ser Ser Thr Ala Gly
                485                 490                 495

Lys Ser Gly Cys Pro Asp Gly Trp Phe Glu Val Asp Glu Asn Cys Val
                500                 505                 510

Tyr Val Thr Ser Lys Gln Arg Ala Trp Glu Arg Ala Gln Gly Val Cys
            515                 520                 525

Thr Asn Met Ala Ala Arg Leu Ala Val Leu Asp Lys Asp Val Ile Pro
        530                 535                 540

Asn Ser Leu Thr Glu Thr Leu Arg Gly Lys Gly Leu Thr Thr Thr Trp
545                 550                 555                 560
```

-continued

```
Ile Gly Leu His Arg Leu Asp Ala Glu Lys Pro Phe Ile Trp Glu Leu
            565                 570                 575

Met Asp Arg Ser Asn Val Val Leu Asn Asp Asn Leu Thr Phe Trp Ala
            580                 585                 590

Ser Gly Glu Pro Gly Asn Glu Thr Asn Cys Val Tyr Met Asp Ile Gln
            595                 600                 605

Asp Gln Leu Gln Ser Val Trp Lys Thr Lys Ser Cys Phe Gln Pro Ser
610                 615                 620

Ser Phe Ala Cys Met Met Asp Leu Ser Asp Arg Asn Lys Ala Lys Cys
625                 630                 635                 640

Asp Asp Pro Gly Ser Leu Glu Asn Gly His Ala Thr Leu His Gly Gln
            645                 650                 655

Ser Ile Asp Gly Phe Tyr Ala Gly Ser Ser Ile Arg Tyr Ser Cys Glu
            660                 665                 670

Val Leu His Tyr Leu Ser Gly Thr Glu Thr Val Thr Cys Thr Thr Asn
            675                 680                 685

Gly Thr Trp Ser Ala Pro Lys Pro Arg Cys Ile Lys Val Ile Thr Cys
            690                 695                 700

Gln Asn Pro Pro Val Pro Ser Tyr Gly Ser Val Glu Ile Lys Pro Pro
705                 710                 715                 720

Ser Arg Thr Asn Ser Ile Ser Arg Val Gly Ser Pro Phe Leu Arg Leu
            725                 730                 735

Pro Arg Leu Pro Leu Pro Leu Ala Arg Ala Ala Lys Pro Pro Pro Lys
            740                 745                 750

Pro Arg Ser Ser Gln Pro Ser Thr Val Asp Leu Ala Ser Lys Val Lys
            755                 760                 765

Leu Pro Glu Gly His Tyr Arg Val Gly Ser Arg Ala Ile Tyr Thr Cys
            770                 775                 780

Glu Ser Arg Tyr Tyr Glu Leu Leu Gly Ser Gln Gly Arg Arg Cys Asp
785                 790                 795                 800

Ser Asn Gly Asn Trp Ser Gly Arg Pro Ala Ser Cys Ile Pro Val Cys
            805                 810                 815

Gly Arg Ser Asp Ser Pro Arg Ser Pro Phe Ile Trp Asn Gly Asn Ser
            820                 825                 830

Thr Glu Ile Gly Gln Trp Pro Trp Gln Ala Gly Ile Ser Arg Trp Leu
            835                 840                 845

Ala Asp His Asn Met Trp Phe Leu Gln Cys Gly Gly Ser Leu Leu Asn
850                 855                 860

Glu Lys Trp Ile Val Thr Ala Ala His Cys Val Thr Tyr Ser Ala Thr
865                 870                 875                 880

Ala Glu Ile Ile Asp Pro Asn Gln Phe Lys Met Tyr Leu Gly Lys Tyr
            885                 890                 895

Tyr Arg Asp Asp Ser Arg Asp Asp Tyr Val Gln Val Arg Glu Ala
            900                 905                 910

Leu Glu Ile His Val Asn Pro Asn Tyr Asp Pro Gly Asn Leu Asn Phe
            915                 920                 925

Asp Ile Ala Leu Ile Gln Leu Lys Thr Pro Val Thr Leu Thr Thr Arg
            930                 935                 940

Val Gln Pro Ile Cys Leu Pro Thr Asp Ile Thr Thr Arg Glu His Leu
945                 950                 955                 960

Lys Glu Gly Thr Leu Ala Val Val Thr Gly Trp Gly Leu Asn Glu Asn
            965                 970                 975

Asn Thr Tyr Ser Glu Thr Ile Gln Gln Ala Val Leu Pro Val Val Ala
```

```
                980             985             990
Ala Ser Thr Cys Glu Glu Gly Tyr Lys Glu Ala Asp Leu Pro Leu Thr
        995            1000            1005
Val Thr Glu Asn Met Phe Cys Ala Gly Tyr Lys Lys Gly Arg Tyr Asp
       1010            1015            1020
Ala Cys Ser Gly Asp Ser Gly Gly Pro Leu Val Phe Ala Asp Asp Ser
1025            1030            1035            1040
Arg Thr Glu Arg Arg Trp Val Leu Glu Gly Ile Val Ser Trp Gly Ser
                1045            1050            1055
Pro Ser Gly Cys Gly Lys Ala Asn Gln Tyr Gly Gly Phe Thr Lys Val
            1060            1065            1070
Asn Val Phe Leu Ser Trp Ile Arg Gln Phe Ile
        1075            1080

<210> SEQ ID NO 7
<211> LENGTH: 3438
<212> TYPE: DNA
<213> ORGANISM: Carcinoscorpius rotundicauda

<400> SEQUENCE: 7
gtgaaggtaa cttaagtatg gtcttagcgt cgttttggt gtctggttta gttctagggc    60
tactagccca aaaatgcgc ccagttcagt ccaaaggagt agatctaggc ttgtgtgatg   120
aaacgaggtt cgagtgtaag tgtggcgatc caggctatgt gttcaacatt ccagtgaaac   180
aatgtacata cttttatcga tggaggccgt attgtaaacc atgtgatgac ctggaggcta   240
aggatatttg tccaaagtac aaacgatgtc aagagtgtaa ggctggtctt gatagttgtg   300
ttacttgtcc acctaacaaa tatggtactt ggtgtagcgg tgaatgtcag tgtaagaatg   360
gaggtatctg tgaccagagg acaggagctt gtgcatgtcg tgacagatat gaagggtgc   420
actgtgaaat tctcaaaggt tgtcctcttc ttccatcgga ttctcaggtt caggaagtca   480
gaaatccacc agataatccc caaactattg actacagctg ttcaccaggg ttcaagctta   540
agggtatggc acgaattagc tgtctcccaa atggacagtg gagtaacttt ccacccaaat   600
gtattcgaga atgtgccatg gtttcatctc cagaacatgg gaaagtgaat gctcttagtg   660
gtgatatgat agaagggct actttacggt tctcatgtga tagtccctac tacttgattg   720
gtcaagaaac attaacctgt caggtaatgg tcagtggaa tggacagata ccacaatgta   780
agaacttggt cttctgtcct gacctggatc ctgtaaacca tgctgaacac aaggttaaaa   840
ttggtgtgga acaaaaatat ggtcagtttc ctcaaggcac tgaagtgacc tatacgtgtt   900
cgggtaacta cttcttgatg ggttttgaca ccttaaaatg taaccctgat gggtcttggt   960
caggatcaca gccatcctgt gttaaagtgg cagacagaga ggtcgactgt gacagtaaag  1020
ctgtagactt cttggatgat gttggtgaac ctgtcaggat ccactgtcct gctggctgtt  1080
cttttgacagc tggtactgtg tgggtacag ccatatacca tgaactttcc tcagtgtgtc  1140
gtgcagccat ccatgctggc aagcttccaa actctggagg agcggtgcat gttgtgaaca  1200
atggccccta ctcggacttt ctgggtagtg acctgaatgg gataaaatcg gaagagttga  1260
agtctcttgc ccggagtttc cgattcgatt atgtccgttc ctccacagca ggtaaatcag  1320
gatgtcctga tggatggttt gaggtagacg agaactgtgt gtacgttaca tcaaaacaga  1380
gagcctggga aagagctcaa ggtgtgtgta ccaatatggc tgctcgtctt gctgtgctgg  1440
acaaagatgt aattccaaat tcgttgactg agactctacg agggaagggg ttaacaacca  1500
cgtggatagg attgcacaga ctagatgctg agaagccctt tatttgggag ttaatggatc  1560
```

-continued

```
gtagtaatgt ggttctgaat gataacctaa cattctgggc ctctggcgaa cctggaaatg    1620
aaactaactg tgtatatatg gacatccaag atcagttgca gtctgtgtgg aaaaccaagt    1680
catgttttca gccctcaagt tttgcttgca tgatggatct gtcagacaga aataaagcca    1740
aatgcgatga tcctggatca ctggaaaatg acacgccac  acttcatgga caaagtattg    1800
atgggttcta tgctggttct tctataaggt acagctgtga ggttctccac tacctcagtg    1860
gaactgaaac cgtaacttgt acaacaaatg gcacatggag tgctcctaaa cctcgatgta    1920
tcaaagtcat cacctgccaa acccccctg  taccatcata tggttctgtg gaaatcaaac    1980
ccccaagtcg acaaactcg  ataagtcgtg ttgggtcacc tttcttgagg ttgccacggt    2040
taccccctccc attagctaga gcagccaaac ctcctccaaa acctagatcc tcacaaccct    2100
ctactgtgga cttggcttct aaagttaaac tacctgaagg tcattaccgg gtagggtctc    2160
gagccatcta cacgtgcgag tcgagatact acgaactact ggatctcaa  ggcagaagat    2220
gtgactctaa tggaaactgg agtggtcggc cagcgagctg tattccagtt tgtggacggt    2280
cagactctcc tcgttctcct tttatctgga atgggaattc tacagaaata ggtcagtggc    2340
cgtggcaggc aggaatctct agatggcttg cagaccacaa tatgtggttt ctccagtgtg    2400
gaggatctct attgaatgag aaatggatcg tcactgctgc ccactgtgtc acctactctg    2460
ctactgctga gattattgac cccaatcagt ttaaaatgta tctgggcaag tactaccgtg    2520
atgacagtag agacgatgac tatgtacaag taagagaggc tcttgagatc cacgtgaatc    2580
ctaactacga ccccggcaat ctcaactttg acatagccct aattcaactg aaaactcctg    2640
ttactttgac aacacgagtc caaccaatct gtctgcctac tgacatcaca acaagagaac    2700
acttgaagga gggaacatta gcagtggtga caggttgggg tttgaatgaa aacaacacct    2760
attcagagac gattcaacaa gctgtgctac ctgttgttgc agccagcacc tgtgaagagg    2820
ggtacaagga agcagactta ccactgacag taacagagaa catgttctgt gcaggttaca    2880
agaagggacg ttatgatgcc tgcagtgggg acagtggagg acctttagtg tttgctgatg    2940
attcccgtac cgaaaggcgg tgggtcttgg aagggattgt cagctgggc  agtcccagtg    3000
gatgtggcaa ggcgaaccag tacgggggct tcactaaagt taacgttttc ctgtcatgga    3060
ttaggcagtt catttgaaac tgatctaaat attttaagca tggttataaa cgtcttgttt    3120
cctattattg ctttactagt ttaacccata agaaggttaa ctgggtaagg cacaaggatc    3180
attgtttctg tttgttttta caaatggtta ttttagtcag tgaatgagaa tagtatccat    3240
tgaagactgt tacctttat  tctacctttt tatattacta tgtaagtatt tgggatatct    3300
tctacacatg aaaattctgt cattttacca taaatttggt ttctggtgtg tgctaagtcc    3360
accagtagag aacgatgtaa ttttcactag cacatgaaat aaatatagaa caaatctatt    3420
ataaactacc ttaaaaaa                                                  3438
```

<210> SEQ ID NO 8
<211> LENGTH: 1019
<212> TYPE: PRT
<213> ORGANISM: Carcinoscorpius rotundicauda

<400> SEQUENCE: 8

```
Met Val Leu Ala Ser Phe Leu Val Ser Gly Leu Val Leu Gly Leu Leu
 1               5                  10                  15

Ala Gln Lys Met Arg Pro Val Gln Ser Lys Gly Val Asp Leu Gly Leu
            20                  25                  30
```

-continued

```
Cys Asp Glu Thr Arg Phe Glu Cys Lys Cys Gly Asp Pro Gly Tyr Val
        35                  40                  45

Phe Asn Ile Pro Val Lys Gln Cys Thr Tyr Phe Tyr Arg Trp Arg Pro
50                  55                  60

Tyr Cys Lys Pro Cys Asp Asp Leu Glu Ala Lys Asp Ile Cys Pro Lys
65                  70                  75                  80

Tyr Lys Arg Cys Gln Glu Cys Lys Ala Gly Leu Asp Ser Cys Val Thr
                    85                  90                  95

Cys Pro Pro Asn Lys Tyr Gly Thr Trp Cys Ser Gly Glu Cys Gln Cys
                100                 105                 110

Lys Asn Gly Gly Ile Cys Asp Gln Arg Thr Gly Ala Cys Ala Cys Arg
                115                 120                 125

Asp Arg Tyr Glu Gly Val His Cys Glu Ile Leu Lys Gly Cys Pro Leu
130                 135                 140

Leu Pro Ser Asp Ser Gln Val Gln Val Arg Asn Pro Pro Asp Asn
145                 150                 155                 160

Pro Gln Thr Ile Asp Tyr Ser Cys Ser Pro Gly Phe Lys Leu Lys Gly
                    165                 170                 175

Met Ala Arg Ile Ser Cys Leu Pro Asn Gly Gln Trp Ser Asn Phe Pro
                180                 185                 190

Pro Lys Cys Ile Arg Glu Cys Ala Met Val Ser Ser Pro Glu His Gly
        195                 200                 205

Lys Val Asn Ala Leu Ser Gly Asp Met Ile Glu Gly Ala Thr Leu Arg
        210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Asn Gly Gln Ile Pro Gln Cys Lys Asn
                    245                 250                 255

Leu Val Phe Cys Pro Asp Leu Asp Pro Val Asn His Ala Glu His Lys
                260                 265                 270

Val Lys Ile Gly Val Glu Gln Lys Tyr Gly Gln Phe Pro Gln Gly Thr
        275                 280                 285

Glu Val Thr Tyr Thr Cys Ser Gly Asn Tyr Phe Leu Met Gly Phe Asp
        290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                    325                 330                 335

Asp Phe Leu Asp Asp Val Gly Glu Pro Val Arg Ile His Cys Pro Ala
                340                 345                 350

Gly Cys Ser Leu Thr Ala Gly Thr Val Trp Gly Thr Ala Ile Tyr His
        355                 360                 365

Glu Leu Ser Ser Val Cys Arg Ala Ala Ile His Ala Gly Lys Leu Pro
        370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Glu Leu Lys Ser
                    405                 410                 415

Leu Ala Arg Ser Phe Arg Phe Asp Tyr Val Arg Ser Ser Thr Ala Gly
                420                 425                 430

Lys Ser Gly Cys Pro Asp Gly Trp Phe Glu Val Asp Glu Asn Cys Val
        435                 440                 445

Tyr Val Thr Ser Lys Gln Arg Ala Trp Glu Arg Ala Gln Gly Val Cys
```

-continued

```
            450                 455                 460
Thr Asn Met Ala Ala Arg Leu Ala Val Leu Asp Lys Asp Val Ile Pro
465                 470                 475                 480

Asn Ser Leu Thr Glu Thr Leu Arg Gly Lys Gly Leu Thr Thr Thr Trp
                485                 490                 495

Ile Gly Leu His Arg Leu Asp Ala Glu Lys Pro Phe Ile Trp Glu Leu
                500                 505                 510

Met Asp Arg Ser Asn Val Val Leu Asn Asp Asn Leu Thr Phe Trp Ala
            515                 520                 525

Ser Gly Glu Pro Gly Asn Glu Thr Asn Cys Val Tyr Met Asp Ile Gln
530                 535                 540

Asp Gln Leu Gln Ser Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Ser Leu Glu Asn Gly His Ala Thr Leu His Gly Gln
                580                 585                 590

Ser Ile Asp Gly Phe Tyr Ala Gly Ser Ser Ile Arg Tyr Ser Cys Glu
            595                 600                 605

Val Leu His Tyr Leu Ser Gly Thr Glu Thr Val Thr Cys Thr Thr Asn
            610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
                645                 650                 655

Ser Arg Thr Asn Ser Ile Ser Arg Val Gly Ser Pro Phe Leu Arg Leu
                660                 665                 670

Pro Arg Leu Pro Leu Pro Leu Ala Arg Ala Ala Lys Pro Pro Pro Lys
            675                 680                 685

Pro Arg Ser Ser Gln Pro Ser Thr Val Asp Leu Ala Ser Lys Val Lys
            690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
                725                 730                 735

Ser Asn Gly Asn Trp Ser Gly Arg Pro Ala Ser Cys Ile Pro Val Cys
                740                 745                 750

Gly Arg Ser Asp Ser Pro Arg Ser Pro Phe Ile Trp Asn Gly Asn Ser
                755                 760                 765

Thr Glu Ile Gly Gln Trp Pro Trp Gln Ala Gly Ile Ser Arg Trp Leu
            770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Asn Gln Phe Lys Met Tyr Leu Gly Lys Tyr
                820                 825                 830

Tyr Arg Asp Asp Ser Arg Asp Asp Tyr Val Gln Val Arg Glu Ala
                835                 840                 845

Leu Glu Ile His Val Asn Pro Asn Tyr Asp Pro Gly Asn Leu Asn Phe
850                 855                 860

Asp Ile Ala Leu Ile Gln Leu Lys Thr Pro Val Thr Leu Thr Thr Arg
865                 870                 875                 880
```

```
Val Gln Pro Ile Cys Leu Pro Thr Asp Ile Thr Thr Arg Glu His Leu
            885             890                     895

Lys Glu Gly Thr Leu Ala Val Val Thr Gly Trp Gly Leu Asn Glu Asn
            900             905                 910

Asn Thr Tyr Ser Glu Thr Ile Gln Gln Ala Val Leu Pro Val Val Ala
        915             920                 925

Ala Ser Thr Cys Glu Glu Gly Tyr Lys Glu Ala Asp Leu Pro Leu Thr
        930             935                 940

Val Thr Glu Asn Met Phe Cys Ala Gly Tyr Lys Lys Gly Arg Tyr Asp
945             950                 955                     960

Ala Cys Ser Gly Asp Ser Gly Gly Pro Leu Val Phe Ala Asp Asp Ser
            965             970                     975

Arg Thr Glu Arg Arg Trp Val Leu Glu Gly Ile Val Ser Trp Gly Ser
            980             985                     990

Pro Ser Gly Cys Gly Lys Ala Asn Gln Tyr Gly Gly Phe Thr Lys Val
            995             1000                1005

Asn Val Phe Leu Ser Trp Ile Arg Gln Phe Ile
    1010            1015
```

METHODS AND REAGENTS FOR DETECTING ENDOTOXIN

This application claims the benefit of and incorporates by reference provisional application Ser. No. 60/310,125 filed Jun. 28, 2001 now abandoned.

FIELD OF THE INVENTION

The invention relates to reagents and methods for detecting endotoxin.

BACKGROUND OF THE INVENTION

Gram negative bacterial endotoxin is a widespread contaminant of a variety of materials, such as water, food, pharmaceutical products, and parenteral preparations. The most commonly used tests for endotoxin contamination employ amebocyte lysates derived from horseshoe crab hemolymph. As populations of these animals decreases, however, it becomes increasingly important to develop rapid and reliable methods for detecting endotoxin that do not rely on the availability of horseshoe crab hemolymph.

BRIEF SUMMARY OF THE INVENTION

The invention provides reagents and methods for detecting endotoxin. One embodiment of the invention is a reagent for detecting endotoxin, comprising a purified horseshoe crab Factor C protein and a surfactant. The surfactant can be an amphoteric surfactant represented by the following formulae:

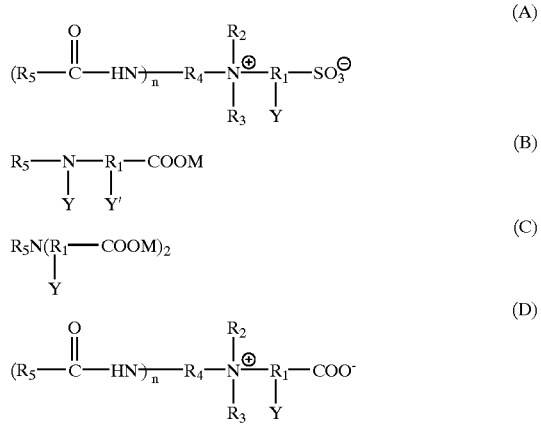

wherein $R_1$ is an alkylene radical having from 1 to 4 carbon atoms; Y and Y' are each (1) hydrogen, (2) lower alkyl, or (3) hydroxy lower alkyl; $R_2$ and $R_3$ are each (1) lower alkyl or (2) hydroxy lower alkyl; n is 0 or 1, when n is 0, $R_4$ is alkyl containing from about 8 to about 18 carbon atoms; when n is 1, $R_4$ is an alkylene radical having from 1 to about 6 carbon atoms; $R_5$ is an alkyl containing from about 8 to about 18 carbon atoms; and M is hydrogen, sodium, potassium or ammonium. The surfactant can be an anionic surfactant represented by the following formulae:

wherein $R_5$, Y, and M have the same meaning as set forth above; $R_6$ is an alkyl from 8 to 24 carbon atoms; n1 is an integer from 1 to 3; n2 is 1 or 2; and Ar is phenyl or naphthyl. The surfactant can be a cationic surfactant represented by the following formula:

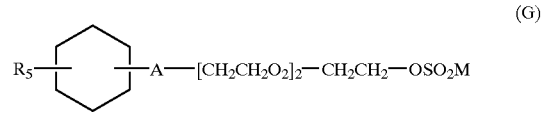

wherein $R_5$, Y, and Y' have the same meaning as set forth above. The surfactant can be a nonionic surfactant represented by the following formula:

wherein $R_5$, Y, and Y' have the same meaning as set forth above and $R_7$ and $R_8$ are each methyl or ethyl. The surfactant can be those nonionic surfactants selected from the group consisting of the condensation product of about 10 to 30 moles of ethylene oxide with the monoester of a hexahydric alcohol containing 6 carbon atoms with the ester group containing 10 to 20 carbon atoms.

Even another embodiment of the invention is a method of detecting endotoxin in a test sample. A test sample is contacted with (1) a reagent comprising (a) a purified horseshoe crab Factor C protein and (b) a surfactant to form a test sample-reagent mixture and (2) a Factor C substrate to form a contacted test sample. Cleavage of the Factor C substrate generates a detectable signal. The contacted test sample is assayed for the presence or absence of the detectable signal. An amount of the detectable signal that is increased relative to a control sample that does not contain endotoxin indicates a presence of endotoxin in the test sample.

A further embodiment of the invention is a method of detecting endotoxin in a test sample. A test sample is contacted with (1) a reagent comprising (a) a recombinant *Carcinoscorpius rotundicauda* Factor C protein and (b) a surfactant and (2) N-t-BOC-Asp(Obzl)-Pro-Arg-7-Amido-4-methyl coumarin to form a contacted test sample. The Factor C protein is made by the method of culturing a host cell comprising a vector encoding the Factor C protein in a supernatant under conditions such that the Factor C protein is expressed into the supernatant. The contacted test sample is assayed for the presence or absence of a fluorescent signal. An amount of the detectable signal that is increased relative to a control sample that does not contain endotoxin indicates a presence of endotoxin in the test sample.

Another embodiment of the invention is a method of detecting endotoxin in a test sample. A test sample is contacted with a reagent comprising a purified horseshoe crab Factor C protein and a surfactant as described above to form a test sample-reagent mixture. The test sample-reagent mixture is contacted with a Factor C substrate, wherein cleavage of the Factor C substrate generates a detectable signal. The contacted test sample-reagent mixture is assayed for the presence or absence of the detectable signal. An amount of the detectable signal that is increased relative to a control sample that does not contain endotoxin indicates a presence of endotoxin in the test sample.

Even another embodiment of the invention is a method of detecting endotoxin in a test sample. A test sample is contacted with a reagent comprising a recombinant *Carcinoscorpius rotundicauda* Factor C protein and a surfactant. The Factor C protein is made by the method of culturing a host cell comprising a vector encoding the Factor C protein in a supernatant under conditions such that the Factor C protein is expressed into the supernatant. The test sample-reagent mixture is contacted with N-t-BOC-Asp(Obzl)-Pro-Arg-7-Amido-4-methyl coumarin. The contacted test sample-regent mixture is assayed for the presence or absence of a fluorescent signal. An amount of the fluorescent signal that is increased relative to a control sample that does not contain endotoxin indicates a presence of endotoxin in the test sample.

Yet another embodiment of the invention is a kit for detecting endotoxin. The kit comprises a reagent that comprises (a) a purified horseshoe crab Factor C protein and (b) a surfactant as described above, together with instructions for a method of detecting endotoxin in a test sample. The method comprises the steps of (1) contacting a test sample with a reagent comprising (a) a purified horseshoe crab Factor C protein and (b) a surfactant as described above to form a test sample-reagent mixture; (2) contacting the test sample-reagent mixture with a Factor C substrate, wherein cleavage of the Factor C substrate generates a detectable signal; and (3) assaying the contacted test sample-reagent mixture for the presence or absence of the detectable signal, wherein an amount of the detectable signal that is increased relative to a control sample that does not contain endotoxin indicates a presence of endotoxin in the test sample.

DETAILED DESCRIPTION OF THE INVENTION

Figure 1:
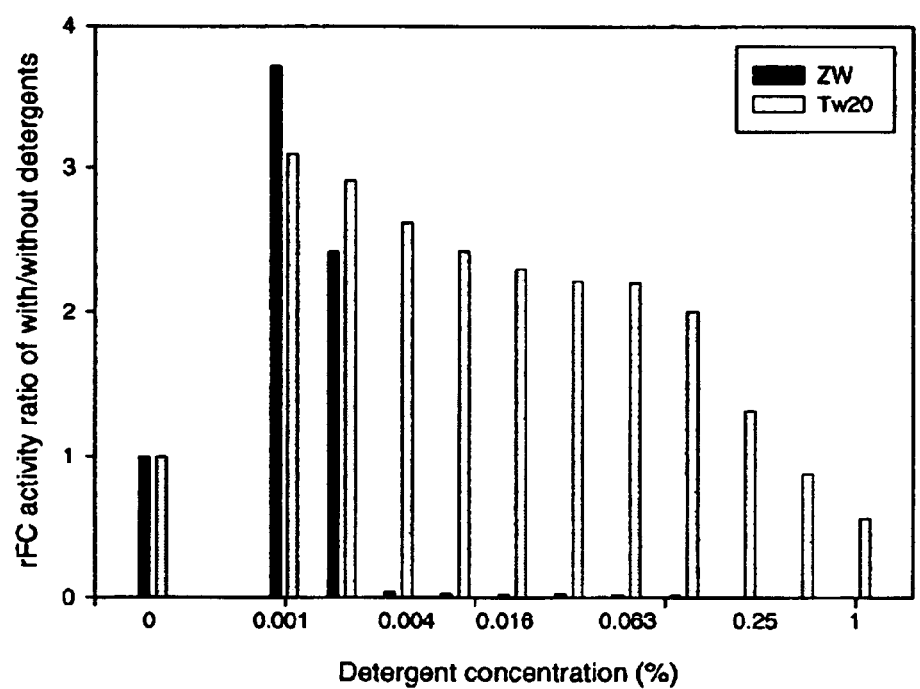
FIG. 1. Graph showing effect of Zwittergent 3-14 and Tween 20 on recombinant Factor C activity.
Figure 2:
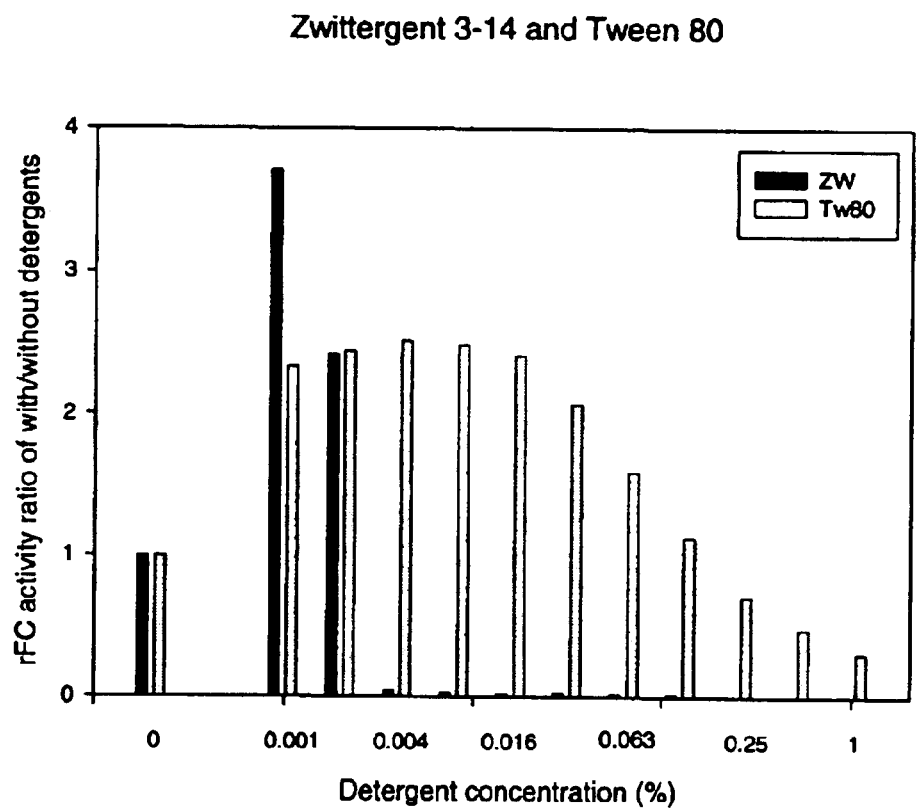
FIG. 2. Graph showing effect of Zwittergent 3-14 and Tween 80 on recombinant Factor C activity.
Figure 3:
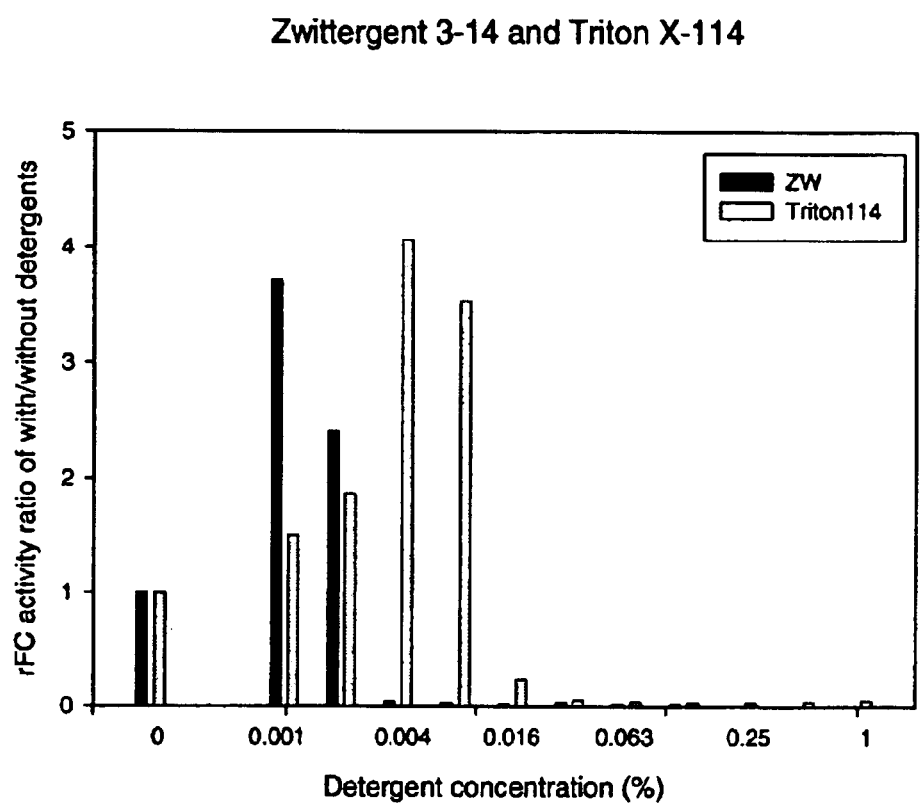
FIG. 3. Graph showing effect of Zwittergent 3-14 and Triton X-114 on recombinant Factor C activity.

The invention is a reagent for detecting endotoxin and a method of using the reagent. The reagent comprises a purified horseshoe crab Factor C protein and a surfactant. This reagent can be used in conjunction with a substrate for Factor C that, upon cleavage, generates a detectable signal to detect endotoxin in a test sample. The presence of the surfactant enhances the activation of the purified Factor C by endotoxin by as much as 3–7-fold, permitting more rapid and sensitive measurement of endotoxin levels in a test sample. The reagent preferably contains a recombinant Factor C, thus eliminating the need for a continuous supply of horseshoe crab hemolymph.

Purified Factor C

One component of the reagent of this invention comprises a purified horseshoe crab Factor C protein. Purified native Factor C from any of the four known horseshoe crab species, *Limulus polyphemus, Carcinoscorpius rotundicauda, Tachypleudus tridentata*, or *Tachypleudus gigas*, can be used in the practice of the invention. The native Factor C can be purified biochemically or purified Factor C can be produced recombinantly.

"Purified Factor C" as used herein means a composition of a Factor C protein as defined hereinafter that contains less than 30% by weight of non-Factor C native amebocyte lysate components from any of the four known horseshoe crab species. The composition specifically includes a cell culture supernatant which comprises recombinant Factor C protein (see below). Methods for purifying horseshoe crab Factor C from its native source are known and are disclosed, for example, in Nakamura et al., *Eur. J Biochem.* 154, 511–21, 1986; Navas et al., *Biochem. Intl.* 21, 805–13, 1990; Tokunaga et al., *J. Biochem.* 109, 150–157, 1991; U.S. Pat. Nos. 5,985,590, and 5,716,834. Any of these methods or their equivalents can be used to obtain a purified Factor C. See also Example 11. Purity of a Factor C preparation can be assessed by any means known in the art, such as SDS gel electrophoresis.

Preferably, the purified Factor C is recombinantly produced. Amino acid sequences for native Factor C from *Tachypleus tridentata* and *Carcinoscorpius rotundicauda* are known, as are the naturally occurring coding sequences for these proteins. SEQ ID NOS:1 and 3 provide coding sequences for the *Tachypleus tridentata* Factor C amino acid sequences shown in SEQ ID NOS:2 and 4, respectively. SEQ ID NOS:5 and 7 provide coding sequences for the *Carcinoscorpius rotundicauda* Factor C amino acid sequences shown in SEQ ID NOS:6 and 8, respectively. Because of the degeneracy of the genetic code, many other sequences can be envisioned that will encode each of these native Factor C proteins, and the invention specifically contemplates use of any of these coding sequences to produce a purified Factor C.

The invention also encompasses use of purified naturally and non-naturally occurring, i.e., recombinantly produced, Factor C variants, provided that the variants retain a Factor C enzyme activity. Factor C enzyme activity can be assessed using any assay for Factor C enzyme activity known in the art. See, e.g., Tokunaga et al., *J. Biochem.* 109, 150–57 (1991) and Nakamura et al., *Eur. J. Biochem.* 176, 89–94, 1988. The endotoxin assays described in Examples 1 and 13, below, also can be used. Naturally occurring Factor C variants include, for example, products of Factor C mRNA splice variants or mutated Factor C genes.

Non-naturally occurring Factor C variants can be constructed using base substitutions, additions, or deletions to produce proteins having Factor C activity. Non-naturally occurring Factor C variants can differ from naturally occurring Factor C by as much as 50, 75, 80, 85, 90, 95, 97, 98, or 99%, as determined using the Blast2 alignment program (Blosum62, Expect 10, standard genetic codes). Fragments of native and recombinantly produced Factor C that retain Factor C activity also can be used in the practice of the invention. Thus, "Factor C" as used herein includes naturally and non-naturally occurring proteins and protein fragments that have the properties described above.

Methods of producing proteins recombinantly are well known in the art and generally involve culturing a host cell comprising an expression vector encoding the Factor C protein in a supernatant under conditions such that the protein is expressed. The expressed protein can be recovered or, preferably, the supernatant comprising the expressed protein is used directly as the source of recombinant Factor C. Thus, "purified Factor C" specifically includes a supernatant which comprises recombinant Factor C. Host cells useful for the production of recombinant Factor C include, without limitation, yeast cells and insect cells. Recombinant production of *Carcinoscorpius rotundicauda* Factor C in *Pichia pastoris* and *Saccharomyces cerevisiae* host cells is specifically disclosed in U.S. Pat. No. 5,985,590.

A particularly preferred method of obtaining recombinant Factor C is to produce the protein in a baculovirus system, as described in Examples 2–5. Briefly, a Factor C coding sequence is cloned into pFASTBAC1. The resultant recombinant plasmid is transformed into DH10BAC competent cells that contain a bacmid with a mini-attTn7 target site and a helper plasmid. In the presence of transposition proteins provided by the helper plasmid, the mini-Tn7 transposable element on the pFASTBAC plasmid can transpose to the mini-attTn7 target site on the bacmid. Colonies containing recombinant bacmids are identified by disruption of the lacZa gene. High molecular weight DNA is prepared from selected DH10BAC clones containing the recombinant bacmid. This DNA is then used to transfect Sf9 insect cells, which will then secrete recombinant Factor C. A particularly surprising discovery of the present invention is that culture medium containing the secreted Factor C, which has been separated from the cultured cells, can be used together with a surfactant (described below) as a reagent in endotoxin assays without further purification.

Surfactant

Reagents of the invention also comprise a surfactant. Surfactants useful in the practice of the invention include those described in U.S. Pat. No. 4,322,217, although other surfactants also can be used. Useful surfactants include amphoteric surfactants that contain both an anionic and cationic group in their structure. Illustrative are the sulfobetaines represented by Formula A:

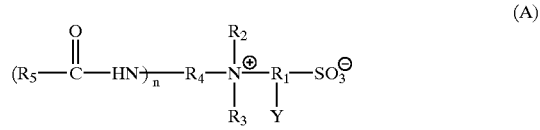

(A)

$R_1$ is an alkylene radical having from 1 to about 4 carbon atoms,

Y is any non-deleterious, chemically suitable substituent including (1) hydrogen, (2) substituted or unsubstituted lower alkyl, e.g., containing 1 to 4 carbon atoms such as methyl, ethyl, propyl, or hydroxy etc.;

$R_2$ and $R_3$ are each selected from substituted or unsubstituted lower alkyl containing 1 to 4 carbon atoms, e.g., such as methyl, ethyl, propyl, hydroxy ethyl, hydroxy methyl, hydroxy propyl, etc.

n=0 or 1, when n=0, $R_4$ is substituted or unsubstituted alkyl, e.g., containing about 8 to about 18 carbon atoms, and when n=1, $R_4$ is an alkylene radical having from about 1 to about 6 carbon atoms, $R_5$ is a substituted or unsubstituted alkyl, e.g., containing about 8 to about 18 carbon atoms.

The term "alkylene" encompasses both polymethylene radicals and other divalent saturated aliphatic radicals. Thus, there may be branching in the linkage provided by the alkylene radical. The term "lower" means a radical containing 1 to 4 carbon atoms.

Sulfobetaines that can be used in the reagent of the present invention are known in the art and have been described as zwitterionic surfactants. The preparation of such compounds is described, for example, in Fernley, *J. Am. Oil Chem. Soc.* 55, 98–103 (1978) and U.S. Pat. No. 3,280,179. In preferred sulfobetaine surfactants, $R_2$ and $R_3$ in the above structure are methyl. It is also preferred that $R_1$ be propylene.

One type of useful sulfobetaine surfactant has the above structure wherein n equals 0 and $R_4$ is an alkyl radical having from about 8 to 18 carbon atoms, preferably a straight chain alkyl radical. For these sulfobetaine surfactants, a convenient source of the $R_4$ component is tallow fatty alcohol, which consists of a mixture of various chain lengths, with a typical composition being approximately 66 percent $C_{18}$, 30 percent $C_{16}$, and 4 percent $C_{14}$ and others. Another convenient source is the middle cut of distilled coconut fatty alcohol, which also consists of a mixture of various chain lengths, with a typical composition being approximately 66 percent $C_{12}$, 23 percent $C_{14}$, 9 percent $C_{16}$ and 2 percent $C_{10}$.

Specific sulfobetaine surfactants of the above structure wherein n equals 0 are set forth in U.S. Pat. No. 3,539,521. A particularly preferred surfactant of this type is N-tetradecyl-N,N-dimethyl-3-ammonio-1-propanesulfonate, which is commercially available from Calbiochem-Behring Corporation under the trademark ZWITTERGENT 3-14.

Another type of useful sulfobetaine surfactant has the above structure wherein n equals 1 and $R_4$ is an alkylene radical having from about 1 to about 6 carbon atoms. In these sulfobetaines wherein n equals 1, $R_5$ is an alkyl radical having from about 8 to about 18 carbon atoms. It is preferred that $R_5$ be straight chain. As previously discussed, convenient sources of alkyl radicals having from about 10 to about 18 carbon atoms are tallow fatty alcohol and coconut fatty alcohol. Specific sulfobetaine surfactants of the above structure wherein n equals 1 are set forth in U.S. Pat. No. 3,280,179.

Particularly preferred sulfobetaine surfactants are 3-(N,N-dimethyl-N-acylamidopropylammonio)-2-hydroxypropane-1-sulfonates, wherein the acyl group is derived from tallow fatty alcohol or coconut fatty alcohol, with coconut fatty alcohol preferred. It will be recognized by those skilled in the art that, in the normal preparation of these derivatives of tallow or coconut fatty alcohols, a mixture of sulfobetaines with varying carbon chain lengths for the acyl groups will result. As previously discussed, these fatty alcohols contain, for the most part, carbon chain lengths that will provide acyl groups with the desired number of carbon atoms, i.e., from about 8 to about 18 carbon atoms. Thus, these mixtures obtained from tallow or coconut fatty alcohols are useful in providing the sulfobetaine surfactant for reagents of the present invention.

A material of this type particularly preferred for use in reagents of the present invention is N-cocoamido-propyl-N,N-dimethyl-N-2-hydroxypropyl sulfobetaine. An example of this is LONZAINE CS, which is commercially available from Lonza, Inc., Fair Lawn, N.J.

Other amphoteric surfactants include the N-long chain alkyl aminocarboxylic acids illustrated by Formula B:

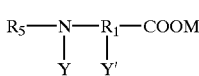 (B)

N-long chain alkyl iminodicarboxylic acids illustrated by Formula C:

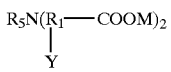 (C)

and N-long chain alkyl or amido betaines illustrated by Formula D:

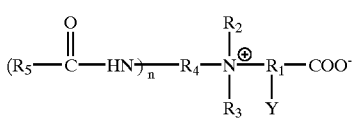 (D)

where $R_1$, $R_2$, $R_3$, $R_4$, Y, and n have the same meaning as they have in Formula A, M is hydrogen or a salt-forming metal, and Y' has the same meaning as Y in Formula A. Y and Y' may be the same or different. Examples of specific amphoteric detergents are N-alkylbeta-aminopropionic acid, N-alkyl-beta-iminodipropionic acid, and N-alkyl-N,N-dimethyl glycine; the alkyl group may be, for example, that derived from coco fatty alcohol, lauryl alcohol, myristyl alcohol (or a lauryl-myristyl mixture), hydrogenated tallow alcohol, cetyl, stearyl, or blends of such alcohols. The substituted aminopropionic and iminodipropionic acids are often supplied in the sodium or other salt forms, which also can be used in reagents of the invention.

Specific examples include cocobetaine sold by Witco Chemical Corporation under the name EMCOL CC 37-18, cocoamidopropyl betaine sold by Lonza Inc. under the name LONZAINE CO, and disodium N-tallow-beta-iminodipropionate sold by Henkel Corporation under the name of DERIPHAT 160.

Examples of other amphoteric detergents are the fatty imidazolines such as those made by reacting a long chain fatty acid (e.g., of 10 to 20 carbon atoms) with diethylene triamine and monohalocarboxylic acids having 2 to 6 carbon atoms, e.g. 1-coco-5-hydroxyethyl-5-carboxymethylimidazoline. Specific examples include cocoimidazoline, which is commercially available under the name AMPHOTERGE K-2 from Lonza, Inc., and capric dicarboxy imidazoline, which is commercially available under the name AMPHOTERGE KJ-2 from Lonza, Inc.

Other examples of useful surfactants include anionic synthetic surfactants, generally described as those compounds that contain hydrophilic and lipophilic groups in their molecular structure and ionize in an aqueous medium to give anions containing both the lipophilic group and hydrophilic group. The alkyl aryl sulfonates, the alkane sulfates, and sulfated oxyethylated alkyl phenols are illustrative of the anionic type of surface active compounds.

The alkyl aryl sulfonates are a class of synthetic anionic surface active agents represented by Formula E:

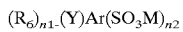 (E)

In Formula E, $R_6$ is a straight or branched chain hydrocarbon radical having from about 1 to about 24 carbon atoms, at least one $R_6$ having at least 8 carbon atoms; n1 is from 1 to 3; n2 is from 1 to 2; Ar is a phenyl or a naphthyl radical, and Y and M have the same meaning as in Formula B. $R_6$ can be, for example, methyl, ethyl, hexyl, octyl, tetraoctyl, iso-octyl, nonyl, decyl, dodecyl, octadecyl, and the like.

Compounds illustrative of the alkyl aryl sulfonates include sodium dodecylbenzene sulfonate, sodium decylbenzene sulfonate, ammonium methyl dodecylbenzene sulfonate, ammonium dodecylbenzene sulfonate, sodium octadecylbenzene sulfonate, sodium nonylbenzene sulfonate, sodium dodecylnaphthalene sulfonate, sodium hetadecylbenzene sulfonate, potassium eicososyl naphthalene sulfonate, ethylamine undecylnaphthalene sulfonate and sodium docosylnaphthalene sulfonate.

The alkyl sulfates are a class of synthetic anionic surface active agents represented by Formula F:

$R_5OSO_3M$ (F)

where $R_5$ and M have the same meaning as in Formula B. Compounds illustrative of alkyl sulfate class of anionic surfactants include sodium octadecyl sulfate, sodium hexadecyl sulfate, sodium dodecyl sulfate, sodium nonyl sulfate, ammonium decyl sulfate, potassium tetradecyl sulfate, diethanolamino octyl sulfate, triethanolamine octadecyl sulfate, and amrnmonium nonyl sulfate.

The sulfated oxyethylated alkylphenols are a class of synthetic anionic surface active agents represented by Formula G:

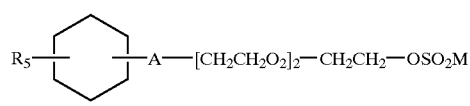 (G)

where A is either oxygen, sulfur, a carbonamide group, a thiocarbonamide group, a carboxylic group, or a thiocarboxylic ester group, z is an integer from 3 to 8, and $R_5$ and M have the same meaning as in Formula B. Compounds illustrative of the sulfated oxyethylated alkyl phenol class of anionic surfactants include ammonium nonylphenoxyl tetraethylenoxy sulfate, sodium dodecylphenoxy triethyleneoxy sulfate, ethanolamine decylphenoxy tetraethyleneoxy sulfate, and potassium octylphenoxy triethyleneoxy sulfate.

Other examples of useful surfactants include nonionic surface active compounds, which can be broadly described as compounds that do not ionize but acquire hydrophilic characteristics from an oxygenated side chain, such as polyoxyethylene; the lipophilic part of the molecule may come from fatty acids, phenol, alcohols, amides, or amines. The compounds are usually made by reacting an alkylene oxide, such as ethylene oxide, butylene oxide, propylene oxide and the like, with fatty acids, straight or branched chain alcohols containing one or more hydroxyl groups, phenols, thiophenols, amides, or amines to form polyoxyalkylene glycoethers and esters, polyoxyalkylene alkylphenols, polyoxyalkylene thiophenols, polyoxyalkylene amides and the like. It is generally preferred to react from about 3 to about 30, more preferably 10 to 30, moles of alkylene oxide per mole of the fatty acids, alcohols, phenols, thiophenols, amides, or amines.

Illustrative of these nonionic surfactants are the products obtained from the reaction of alkylene oxide with an aliphatic alcohol having from 8 to 18 carbon atoms, such as octyl, nonyl, decyl, octadecyl, dodecyl, tetradecyl and the like, with monoesters of hexahydric alcohols, the ester group containing 10 to 20 carbon atoms such as sorbitan monolaureate, sorbitan monooleate and sorbitan monopalmitate, with an alkyl phenol in which the alkyl group contains between 4 and 20 carbon atoms, such as butyl, dibutyl, amyl, octyl, dodecyl, tetradecyl, and the like, or with an alkyl amine in which the alkyl group contains between 1 to 8 carbon atoms.

Compounds illustrative of synthetic nonionic surfactants include the products obtained from condensing ethylene oxide or propylene oxide with the following: propylene glycol, ethylene diamine, diethylene glycol, dodecyl phenol, nonyl phenol, tetradecyl alcohol, N-octadecyl diethanolamide, N-dodecyl monoethanolamide, polyoxyethylene (20) sorbitan monooleate sold under the name TWEEN 80 and polyoxyethylene (20) sorbitan monolaurate sold under the name TWEEN 20.

Other nonionic surfactants include long chain tertiary amine oxides corresponding to Formula H:

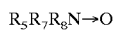

(H)

wherein $R_5$ has the same meaning as in Formula A, and $R_7$ and $R_8$ are each methyl or ethyl radicals. The arrow in the formula is a conventional representation of a semi-polar bond. Examples of amine oxides suitable for use in this invention include dimethyldodecylamine oxide, dimethyloctylamine oxide, dimethyldecylamine oxide, dimethyltridecylamine oxide, and dimethylhexadecylamine oxide.

Cationic surface active agents can also be used as surfactants. Such agents are those surface-active compounds which contain an organic hydrophobic group and a cationic solubilizing group. Typical cationic solubilizing groups are amine and quaternary groups. Such cationic surface-active agents are represented by Formula I:

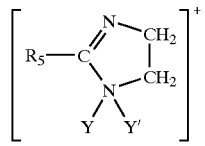

(I)

wherein $R_5$, Y, and Y' have the same meaning as in Formula C.

Other examples of suitable synthetic cationic surfactants include the diamines such as those of Formula J:

(J)

wherein R is an alkyl group of about 12 to 22 carbon atoms, such as N-2-aminoethyl stearyl amine and N-2-aminoethyl myristyl amine; amide-linked amines such as those of Formula K:

(K)

such as N-2-amino ethylstearyl amide and N-amino ethyl myristyl amide; quaternary ammonium compounds wherein typically one of the groups linked to the nitrogen atom are alkyl groups which contain 1 to 3 carbon atoms, including such 1 to 3 carbon alkyl groups bearing inert substituents, such as phenyl groups and there is present an anion such as halogen, acetate, methylsulfate, etc. Typical quaternary ammonium compounds are ethyl-dimethylstearyl ammonium chloride, benzyl-dimethyl-stearyl ammonium chloride, benzyldimethyl-stearyl ammonium chloride, trimethyl stearyl ammonium chloride, trimethylcetyl ammonium bromide, dimethylethyl dilaurylammonium chloride, dimethyl-propyl-myristyl ammonium chloride, and the corresponding methosulfates and acetates.

Another suitable cationic surfactant is represented by Formula L:

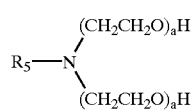

(L)

wherein $R_5$ has the same meaning as in Formula A and each a is an integer from 1 to 15. An example is the polyethylene glycol amine of hydrogenated tallow wherein $R_5$ represents the tallow radical and a+a has an average value of 5.

Other useful surfactants for use in the Factor C-surfactant reagent include Triton X-100, Triton X-114, octyl-beta-D-thioglucoside (OTG, Amresco #J575), Genapol C-100 (an alkyl polyoxyethylene C12E1O; Calbiochem #345794), Tween 20, and Tween 80.

Factor C-Surfactant Reagent

To form a reagent of the invention, purified Factor C and a surfactant are combined in an aqueous solution. A suitable buffer solution for this purpose contains 30 mM Tris, pH 8.0, 30 mM NaCl, and 0.3% lactose. The concentration of purified Factor C in a reagent of the invention preferably ranges from 0.03–3 µg/ml. The concentration of surfactant in the reagent of the invention preferably ranges from 0.001–0.003%. Optimum concentrations of purified Factor C and of the surfactant will vary, depending, for example, on the purity of the Factor C and the particular surfactant. Optimum concentrations of purified Factor C and of surfactant can be determined using routine testing. In the assay exemplified in Examples 1 and 13, the optimal concentration of the surfactant ZWITTERGENT 3-14 is 0.0025%.

Endotoxin Assay

The reagent described above can be used in an assay to detect endotoxin in a test sample. The test sample can be any sample in which it would be useful to detect endotoxin, including water, aqueous solutions such as buffers, pharmaceutical preparations (e.g., vaccines, intravenous fluids, drug preparations), biomedical imaging reagents (e.g., dyes, radioactive solutions), enzyme preparations (e.g., collagenase), tissue culture media, beverages, blood, urine, cerebrospinal fluid, lymph, serum, and solutions formed by incubating water or an aqueous solution with a solid sample, such as a foodstuff or a surgical glove.

Either a two-step or a one-step assay can be performed. To perform the two-step assay (Example 1), a test sample is incubated with a reagent containing purified Factor C and a surfactant, then a Factor C substrate that will generate a detectable signal upon cleavage is added. To perform the one-step assay (Example 13), endotoxin, the reagent containing purified Factor C and a surfactant, and a substrate are added together.

Substrates that will generate a fluorescent signal upon cleavage are particularly preferred, such as N-t-BOC-Asp (Obzl)-Pro-Arg-7-Amido-4-methyl coumarin ("DPR," Bachem 1-1560.0050) and N-t-BOC-Val-Pro-Arg-7-Amido-4-methyl coumarin ("VPR," Bachem 1-1120.0050). Concentrations of DPR generally range from about 10–100 mM, 25–100 mM, 5–100 mM, 75–100 mM, 25–75 mM, 50–75 mM, 25–50 mM, or 50–75 mM. Concentration of VPR generally range from about 50–200 mM, 50–150 mM, 50–100 mM, 50–75 mM, 75–100 mM, or 75–100 mM.

The optimum concentration for a particular substrate varies. For example, the optimum concentration for DPR is 50 mM, whereas the optimum concentration for VPR is 100 mM. Moreover, the particular substrate can be chosen depending on the endotoxin levels expected to be present in the test sample. The VPR substrate has a better linear range at higher endotoxin concentrations, and the DPR substrate has a better linear range at lower endotoxin concentrations. Thus, DPR can be used in assays in which higher sensitivity is desired, whereas VPR is the preferred substrate when higher endotoxin levels are expected to be present and a lower sensitivity is required.

Fluorescence can be measured using any means known in the art. If a fluorimeter is used with the DPR or VPR substrates described above, the excitation is set at 360, 380, 390, or 395 nm (slit width of 5–40 nm) and the emission is measured at 440 or 460 nm (slit width of 2.5–40 nm). Measurement can be either qualitative or quantitative, by reference to a standard endotoxin concentration curve.

The assay can be carried out in a clear vessel, such as a glass or polystyrene tissue culture plate, or can be carried out in a black vessel (e.g., a black 96-well microplate). If desired, the assay can be adapted for high-throughput screening of multiple samples using, for example, 96-well microtiter plates.

Kits

The invention also provides a kit for use in detecting endotoxin. The kit comprises a purified horseshoe crab Factor C protein and a surfactant, as described above. Instructions for using the reagent to detect endotoxin can be included. Kits also can include a Factor C substrate for use in the assay.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Two-Step Endotoxin Assay

Figure 4:
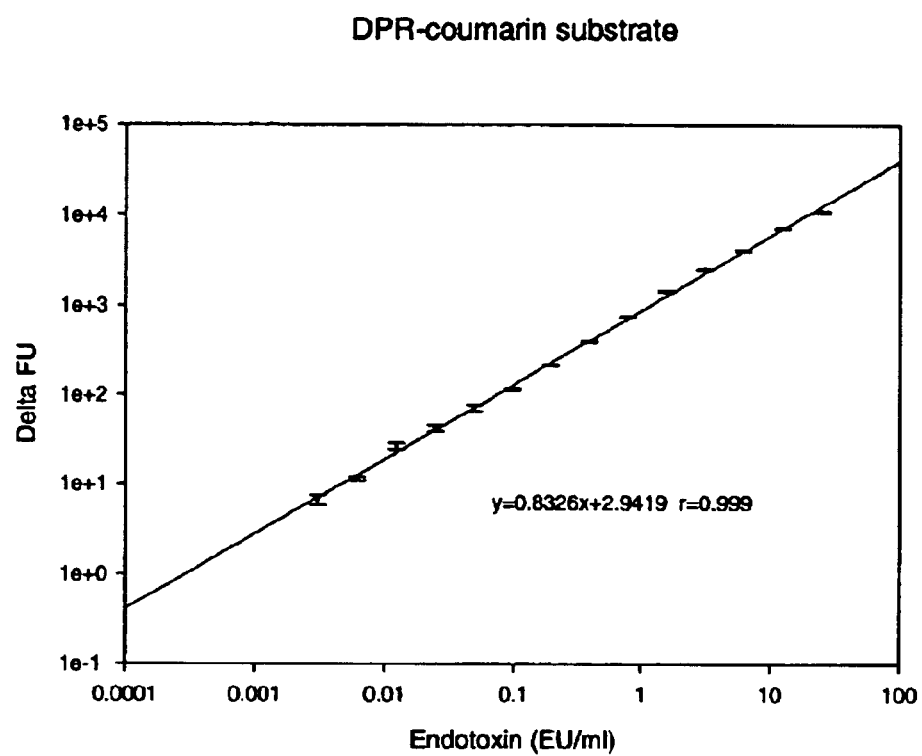
FIG. 4. Plot showing endotoxin detection using a DPR (N-t-BOC-Asp(Obzl)-Pro-Arg-7-Amido-4-methyl)-coumarin substrate.
Figure 5:
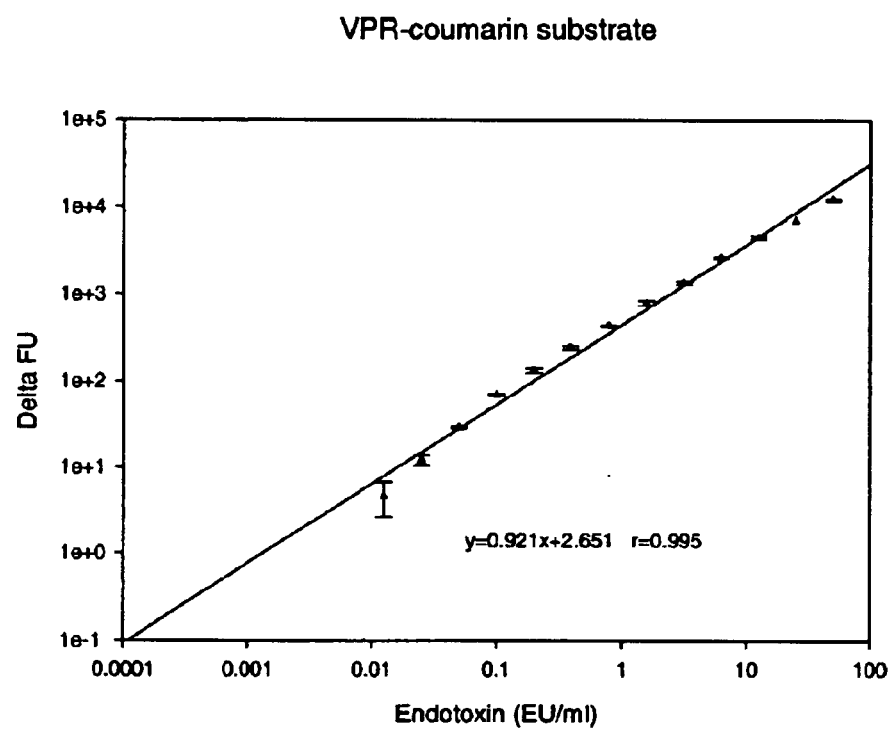
FIG. 5. Plot showing endotoxin detection using a VPR (N-t-BOC-Val-Pro-Arg-7-Amido-4-methyl)-coumarin substrate.

Endotoxin was pre-incubated with culture medium containing recombinant *Carcinoscorpius rotundicauda* Factor C obtained from recombinant Factor C-producing Sf9 cells for 1 hour in assay buffer (30 mM Tris, pH 8.0, 30 mM NaCl, 0.3% lactose, and 0.0025% Zwittergent 3-14). The substrate N-t-Boc-Asp(Obzl)-Pro-Arg-7-Amido-4-methyl coumarin (DPR-coumarin) was added to the mixture to a final concentration of 50 mM. The fluorescence generated from the cleavage of the substrate by activated Factor C was measured after 15–20 minutes. The results are shown in FIG. 4. Results of a similar assay carried out using the substrate N-t-Boc-Val-Pro-Arg-7-Amido-4-methyl coumarin at a final concentration of 100 mM are shown in FIG. 5.

EXAMPLE 2

Transfection of Bacmid DNA-Factor C into Sf9 Cells and Harvesting of Recombinant Viral Supernatant Sf9 cells are seeded at a density of $5 \times 10^6$ per 35 mm well in a 6-well tissue culture plate in insect cell culture medium (ICCM) containing 50 U/ml penicillin and 50 mg/ml streptomycin. Insect-Xpress (BioWhittaker Cat. #04-10270) or Sf-900 SFM are suitable media; however, any comparable medium in which SF9 cells grow can be used. The plates are incubated at 27° C. for 1 hour to allow the cells to settle. Meanwhile, the following are prepared (each per well): (1) 7 mg of bacmid-Factor C DNA in 100 ml ICCM (without antibiotics) and (2) 6 ml CELLFECTIN (Gibco-BRL) plus 100 ml ICCM (without antibiotics). Solutions (1) and (2) are mixed gently and incubated at room temperature for one hour. To this mixture, 0.8 ml of ICCM (without antibiotics) is added.

The adhered Sf9 cells are washed gently with 2 ml ICCM (without antibiotics). One ml of CELLFECTIN-DNA complex is added to each well and incubated at 27° C. for 5 hours. The transfection mixtures are removed completely, and 2 ml of ICCM containing antibiotics is added. After incubation at 27° C. for 96 hours, the cell culture supernatant is harvested. The supernatant is clarified by centrifugation at 5000 rpm for 10 minutes in a SIGMA 3K10 swing-out rotor, Nr. 11133. The supernatant, containing the recombinant baculovirus, is stored at 4° C.

EXAMPLE 3

Amplification of Recombinant Viral Stock

Virus amplification can be done with Sf9 cells either in a monolayer or in suspension. For monolayer culture, the medium is decanted from a culture of 80% confluent one day-old Sf9 cells in a 75 cm² tissue culture flask. The cell monolayer is infected with 1 ml of virus (Example 2) using an MOI of 0.1–1. The virus stock is sterile-filtered using a Millipore GV millex filter (yellow; low-protein binding). Calculation of the viral inoculum is as follows:

$$\text{volume of inoculum} = \frac{MOI \times \text{total cell number}}{\text{virus titer in pfu/ml}}$$

Thus, for $1 \times 10^7$ cells, at a virus titer of $2 \times 10^7$ pfu/ml, the volume of the inoculum is 0.5 ml. The volume of the inoculum is adjusted to 1 ml with ICCM before it is introduced to the cells.

The flask is rocked several times to ensure that the cell monolayer is completely covered by the 1 ml viral inoculum. The flask is then incubated at 27° C. for one hour without rocking. After the incubation, the flask is placed upright, and 14 ml of fresh ICCM is added. The flask is then incubated for 3 days at 27° C.

The culture supernatant is harvested into sterile pyrogen-free tubes and centrifuged at 2000 rpm for 10 minutes at 4° C. using a Sigma 3K10 swing out rotor. For immediate use, the viral stock is stored at 4° C. For long-term storage, the viral stock is placed at −80° C.

For suspension culture, use log-phase grown Sf9 cells with viability >95% for vial amplification. Cell density and viability are determined. Sf9 cells are diluted with fresh InsectXPRESS to $1 \times 10^6$ cells per ml. Virus to be amplified is added to the Sf9 culture, at an MOI of 0.02 (virus/cell), as follows:

$$\text{Vol. of inoculum virus stock (ml)} = \frac{(\text{Total cells/ml}) \times (\text{Total Vol. of culture}) \times (MOI)}{(\text{Virus titer in pfu/ml})}$$

Spinner flasks are incubated for three days at 27° C.+/−2° C., with constant stirring at 90–120 rpm. The cell culture is transferred to sterile centrifuge bottles and centrifuged at 2000 rpm for 10 minutes at 4° C. The supernatant is collected into a sterile container and discard the cell pellet. The supernatant is filtered through a 0.45 μm filter into a sterile container. The supernatant is further filtered through a sterile, 0.2 μm filter into a sterile container. The finished virus stock is stored protected from light at 2–8° C. A titer determination is performed as explained in Example 4.

EXAMPLE 4
Titration of *Baculovirus*

Virus titer (Plaque Forming Units (PFU) per ml) can be determined with plaque assay, end-point dilution, or other viral titer kits (e.g., BacPAK Baculovirus Rapid Titer Kit by Clontech #K1599-1). Plaque assay is performed in immobilized monolayer culture. Plaque assays to be are performed are determined as follows:

Plaque assay number=Number of viral dilution×4 (quadruplicates)+2 positive and 2 negative controls.

For example, $10^5$, $10^6$, $10^7$, $10^8$ for viral dilution, each dilution in quadruplicate wells, would be a 16-well plaque assay. Include two positive controls and two negative controls in the plaque assay, for a total of 20 wells.

Prepare a cell suspension of $5 \times 10^5$ cells per ml density in 10% FBS serum media. Seed 6-well plates at 2 ml per well with above cell suspension. Cells are allowed to attach two hours before experiments. Cells are ~80% confluent.

Prepare 10-fold serial viral dilutions using 4.5 ml media and 0.5 ml of viral stock in sterile 15-ml tubes. Aspirate the medium from each well. Add viral dilution 1 ml per well and incubate at 27° C. for 2 hours.

Warm 1.3× SF-900II (Gibco-BRL #10967-032) to 27° C. Melt 4% agarose (Gibco 18300-012) and keep in 50° C. water-bath. Add 1.3× media and 4% agarose in 3:1 ratio to make 1% agarose in culture media. Keep this agar in a 40° C. water-bath (for example, in a beaker that can be brought to a hood).

Working quickly so that the agarose mixture does not solidify, aspirate the viral solution from the cell monolayers. Add 2 ml 1% agarose to each well. Let the plates sit in the hood with the covers slightly open for 10 minutes. Invert the plates and put them in a sealed box with damp paper towels to provide humidity. Incubate at 27° C. for 5–7 days, or until plaques are well formed.

At day 7 of post-infection, add 0.5 ml 0.033% neutral red (in water), incubate 3 minutes, and discard. Alternatively, add 0.5 ml 0.1% trypan blue (in water), rock to cover, sit 3 minutes, and discard. Incubate the plates for 2 hours. With the help of a light box and a magnifier, count the plaques on each plate. Virus titer is calculated using the following formula:

Virus titer (pfu/ml)=# of plaques×viral dilution.

EXAMPLE 5
Infection of Sf9 Cells for Recombinant Factor C Production in Serum-Free Cultures High viability Sf9 cells are used (e.g., viability of 95–100% in serum-free conditions). Culture log-phase Sf9 cells to a cell density of between $1.5 \times 10^6$ and $2.5 \times 10^6$ cells per ml in suspension culture. Recombinant factor C production also can be carried out by infecting Sf9 cells grown in monolayer culture. Determine cell density and viability. Dilute Sf9 cells with fresh InsectXPRESS to $1.5 \times 10^6$ cells per ml. Add recombinant baculovirus high titer stock to the Sf9 culture, at an MOI of 1 (virus/cell), as follows:

$$\text{Vol. of inoculum } HTS \text{ (ml)} = \frac{(\text{Total cells/ml}) \times (\text{Total Vol. of culture}) \times (MOI)}{(\text{Virus Titer in pfu/ml})}$$

Harvest culture supernatant seventy-two hours post-infection. Transfer the cell culture to sterile centrifuge bottles and centrifuge at 2000 rpm for 10 minutes at 4° C. Collect the supernatant into a sterile container and discard the cell pellet. Filter the supernatant through a 0.45 μm filter into a sterile container. Further filter supernatant through a sterile, 0.2 μm filter into a sterile container. This culture supernatant, which contains recombinant Factor C, can be stored at 4° C. for up to one year and can be used directly to form a reagent for endotoxin detection in accordance with the present invention.

EXAMPLE 6
Culture and Subculture of Sf9 Cells Adapted in Serum-Free Medium

Sf9 cells grow at 27° C. without $CO_2$. Maximal aeration is preferred. If spinner culture bottles are used, loosen the side screw-caps to increase aeration. Sf9 cells adapted to grow in serum-free medium should be subcultured at 4–5 days intervals on a routine basis.

Subculture at $5.0 \times 10^5$ cells/ml in a 250 ml spinner or shake flask containing 100 ml of medium with loosened caps to provide maximal aeration. Stir the culture at 90–100 rpm. Cell viability should be above 90%.

Remove 4–5 day old cultures from the 27° C. incubator and swab with 70% alcohol. Take an aliquot of cell suspension to determine cell viability and total cell count using trypan blue dye. Determine the cell dilution necessary to obtain $5 \times 10^5$ cells/ml. Swirl the stock culture flask several times and remove the appropriate volume of cell suspension based on the calculation. Inoculate a new 250 ml spinner flask containing enough pre-warmed fresh medium necessary to make up the final culture volume to 100 ml. Place the cultures back into the incubator. Set the stirring speed to 90–100 rpm.

EXAMPLE 7
Cryopreservation of Serum-Free Cultures of Sf9 Cells

Grow Sf9 cells either in a monolayer or in suspension. Harvest the cells at mid-log phase of growth (about 2 days) at a viability of >90%. Keep conditioned medium on ice and sterile-filter.

Determine the cell viability using the trypan blue dye exclusion method. Calculate the required volume of cryopreservation medium (7.5% DMSO in 50% fresh serum-free ICCM medium and 50% conditioned medium; sterile-filtered) to yield a final density of $1-2 \times 10^7$ cells/ml. Hold the cryopreservation mixture on ice. Meanwhile, centrifuge cells from the suspension for 3 minutes at 800 rpm/500× g. Discard the sample if a lot of cells are unpelleted and in the supernatant.

Resuspend the cell pellet in the determined volume of chilled cryopreservation mix to obtain $1-2 \times 10^7$ cells/ml. Quickly dispense 1–1.5 ml aliquots of cell suspension into cryovials. Freeze the cells at −70 to −90° C. for 4 hours on the upper gaseous phase of liquid nitrogen. Plunge the vials into liquid nitrogen.

EXAMPLE 8
Recovery of Cryopreserved Serum-Free Sf9 Cells

Thaw vial by rapid agitation in 37° C. water bath just until melted. Remove the vial from the water bath and swab with sterile 70% isopropanol. Open vial, remove contents of the vial into a sterile centrifuge tube of appropriate size; and dilute the cell suspension with 5 volumes of InsectXPRESS medium (or equivalent) that has been equilibrated to 27° C.+/−2° C. in an incubator. Centrifuge the diluted suspension at 125× G for 10 minutes. Discard the fluid and resuspend the cells in a volume of culture medium equal to fluid discarded. Determine cell count and viability. Adjust viable cell density to between $2 \times 10^5$ cells per ml and $3 \times 10^5$ cells per ml using serum free medium. Transfer flask in a 27° C.+/−2° C. incubator on a rotary platform shaker set for continuous shaking and 100–125 revolutions per minute. When the viable cell count of the culture doubles at least every 26 hours, the culture may be expanded as described in Example 6.

EXAMPLE 9
Adaptation of Sf9 Cells to Suspension Culture

Six to ten confluent 75 cm² monolayer T-flasks of Sf9 cells are required to initiate a 100 ml suspension culture. Dislodge cells from the bottom of the flasks by holding a flask in one hand and tapping it against the palm of the other hand. Pool the cell suspension and perform a viability count.

Dilute the cell suspension to approximately $5 \times 10^5$ viable cells/ml at room temperature using complete serum-supplemented or serum-free growth medium contained in a 250 ml spinner flask. The top of the stirrer blade may be slightly above the cell suspension. This provides additional aeration. The side arm caps should be loosened by one-quarter turn.

Incubate the cells at 27° C. at a constant stirring rate of 100 rpm. Subculture when the viable cell count reaches $1–2 \times 10^6$ cells/ml (3–7 days post-seeding), increase stirring speed by 5 rpm per passage until culture viability is >80%. Repeat until a stirring speed of 100 rpm is achieved for the spinner flask or 130–140 rpm is achieved for the shaker flask cultures. At this point, reduce seeding density to $3 \times 10^5$ cells/ml during subculture.

If large clumps of cells persist (e.g., >10 cells per clump), let the spinner/shaker flask stand 2–3 minutes without stirring prior to subculturing. This allows larger clumps to settle to the bottom. Pool the upper one-third of the suspension cells for counting and seeding into new cultures. This procedure selects for a cell population that grows as single cells. It may be necessary to repeat this step 2–3 times until clumping is reduced.

EXAMPLE 10
Effect of Different Detergents and Different Concentrations of Detergents on the Recombinant Factor C Assay Materials and Methods The following reagents were purchased from the manufacturers indicated: Zwittergent 3-14 (Calbiochem, Cat# 693017), Tween 20 (ICN, Cat# 194841), Tween 80 (ICN, Cat# 194842), Triton X-114 (ICN, Cat# 193971), ), n-Octyl-beta-D-thioglycopyranoside (OTG, Amresco, Cat# J575), and Triton X-100 (ICN, Cat# 194854). The recombinant Factor C (rFC) assay was carried out using 20 μl of each detergent (~10× of final concentration), 150 μl of 1 EU/ml EC-6, 10 μl of rFC supernatant 031901I, 20 μl of 300 mM Tris, pH 8.0, and 20 μl of 0.55 mM DPR-coumarin substrate. The results of the assay were read at 38° C. using a Cytofluor reader set at 390/440 nm, 5 minutes per cycle, for 1 hour. The data were graphed after 30 minutes.

Results

As shown in FIGS. 1–3 and 9–11, low concentrations of Zwittergent 3-14, Tween 20, Tween 80, Triton X-114, OTG, Genapol C-100 and Triton X-100 enhanced the rFC assay 2–7 fold. The enhancing concentration range for Zwittergent 3-14, Triton X-114, OTG and Triton X-100 is narrow, while the enhancing concentration range for Tween 20, Tween 80 and Genapol C-100 is wide.

Table 1 summarizes the results obtained by testing nine detergents. These detergents can be divided into three groups: detergents that have a narrow concentration range for enhancing recombinant Factor C activity, detergents that have wide concentration range for enhancing recombinant Factor C activity, and detergents that inhibit recombinant Factor C activity.

TABLE 1

| Detergents | Detergent concentration range for rFC enhancing | Detergent concentration range for rFC inhibition | CMC (mM) | MW | Category |
|---|---|---|---|---|---|
| Group 1 | | | | | |
| Zwittergent | 0.001–<0.004% | >=0.004% | 0.1–0.4 | 363.6 | ZW |
| Triton X-100 | 0.001–<0.008% | >=0.008% | 0.2–0.9 | 631 | Non-ionic |
| Triton X-114 | 0.001–<0.016% | >=0.016% | 0.35 | 537 | Non-ionic |
| OTG | 0.031–<0.5% | >=0.5% | 9 | 308.4 | Non-ionic |
| Group 2 | | | | | |
| Genapol C-100 | 0.001–0.5% | >0.5% | / | 627 | Non-ionic |
| Tween 20 | 0.001–0.5% | >0.5% | 0.059 | 1228 | Non-ionic |
| Tween 80 | 0.001–0.25% | >0.25% | 0.012 | 1310 | Non-ionic |
| Group 3 | | | | | |
| Deoxycholic Acid | / | >=0.0004% | 1.5 | 414.6 | Ionic |
| SDS | / | >=0.0004% | 2.3 | 288.5 | Ionic |

Figure 6:
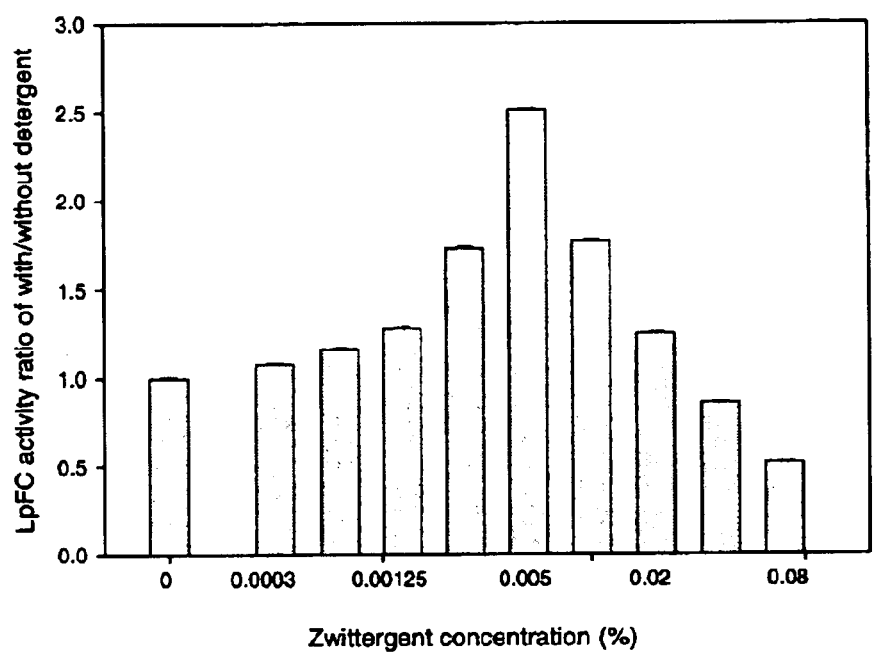
FIG. 6. Graph showing *Limulus* Factor C activity at different Zwittergent concentrations.

The enhancing/inhibiting effect of Zwittergent 3-14 was also tested using purified *Limulus* factor C (FIG. 6). A similar enhancing/inhibiting effect was observed, although the relative factor C activity ratio, the enhancing and inhibiting detergent concentrations were different from those in the recombinant Factor C assay.

EXAMPLE 11
Antisera Against *Limulus* Factor C

We isolated the factor C from *Limulus* and generated antisera against the protein. The *Limulus* lysate was first separated with a S-100 gel filtration followed by cation-ion exchange column. The fractions were assayed for factor C activity using the N-t-BOC-Val-Pro-Arg 7-Amido-4-methyl coumarin substrate. The *Limulus* factor C was purified 73 fold with 80% homogeneity as determined by enzyme assay and SDS-PAGE. The molecular weight of *Limulus* factor C was 117 kDa by SDS-PAGE under non-reducing conditions. Reduced SDS-PAGE showed two major bands of 79 kDa and 40 kDa, corresponding to the heavy and light chain. Tryptic peptide sequencing revealed that the *Limulus* factor C sequence closely matched the Asian species, with >90% sequence identity. A specific polyclonal antibody against the *Limulus* factor C was generated in rabbits. The anti-factor C purified IgG inhibited the activation of factor C by LPS but had no effect on the protease activity once the factor C was activated by LPS. The factor C antisera demonstrated the importance of this protein in the initial recognition of LPS by *Limulus* lysate.

EXAMPLE 12
Increase in Sensitivity in Endotoxin Detection in the Presence of Surfactant A one-step, 1-hour endpoint assay was performed. Endotoxin 055:B5, 0.01, 0.1, 1, and 10 EU/ml were used for the standard curve. Blank and endotoxin standards (100 µl each) were added to a 96-well plate. Recombinant Factor C supematant, assay buffer (150 mM NaCl, 150 mM Tris, pH 8.0, and 1.5% lactose, with or without 0.0125% Zwittergent) and substrate solution (0.2 mM in water) were mixed at 1:4:5 ratios. This mixture was added into each blank and endotoxin standard. The fluorescence was recorded at time zero and time 1 hour. The difference in fluorescences (delta fluorescence) were normalized with the blank. Normalized delta fluorescence was then graphed against endotoxin concentration in a log-log scale. Each data point is the result of duplicate assays.

Figure 7:
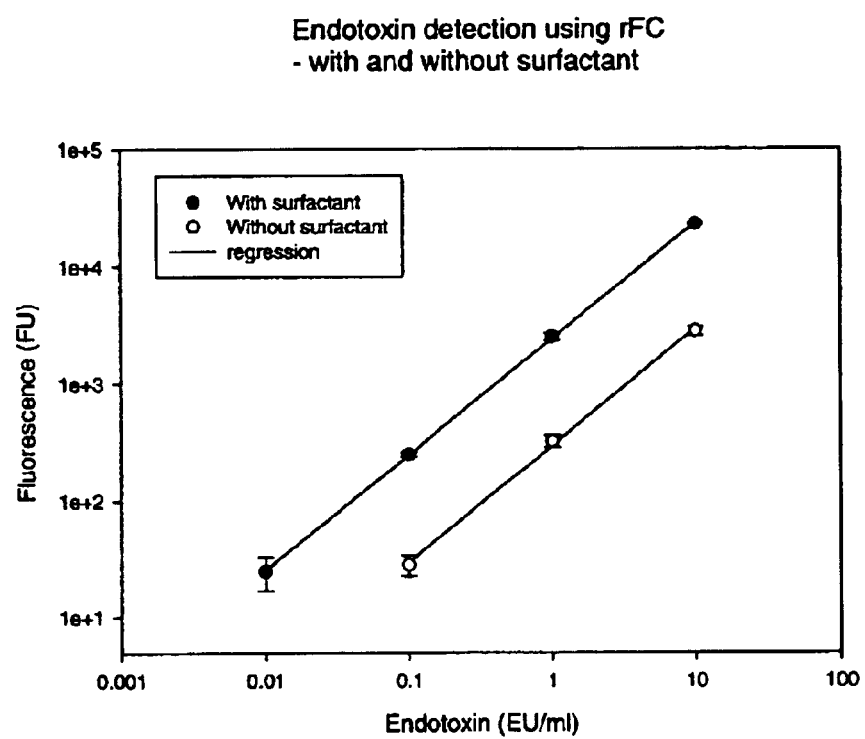
FIG. 7. Graph showing endotoxin sensitivity in the presence and absence of surfactant.

The results are shown in FIG. 7. The endotoxin detection sensitivity increased 10-fold when surfactant was included.

EXAMPLE 13
One-Step Endotoxin Assay

A one-step endotoxin assay can be carried out in a 96-well plate, using 100 µl each of blank and endotoxin standards. One hundred microliters of a mixture of recombinant Factor C supernatant (Baculovirus-infected Sf9 cell culture medium), buffer (150 mM Tri, pH 8.0, 150 mM NaCl, 1.5% beta-lactose, and 0.0125% Zwittergent 3-14) and fluorogenic substrate (DPR-coumarin, 0.2 mM) at a ratio of 1:4:5 is added to wells of the plate. The plate is incubated at 37° C. for 1 hour. Excitation and emission are read at 390 and 440 nm, respectively, in a fluorescence microplate reader.

Figure 8:
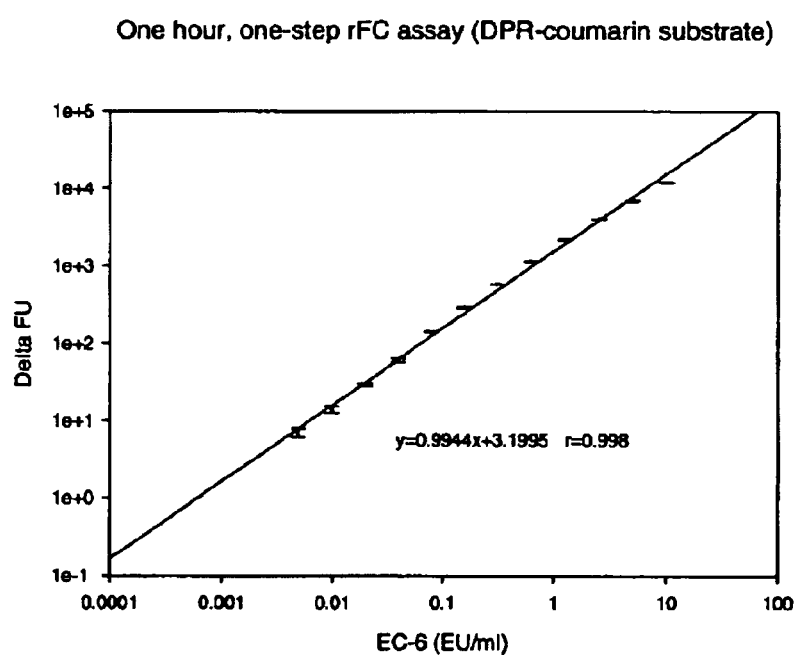
FIG. 8. Graph showing results of a one hour, one-step endotoxin assay, using DPR-coumarin as a substrate.
Figure 9:
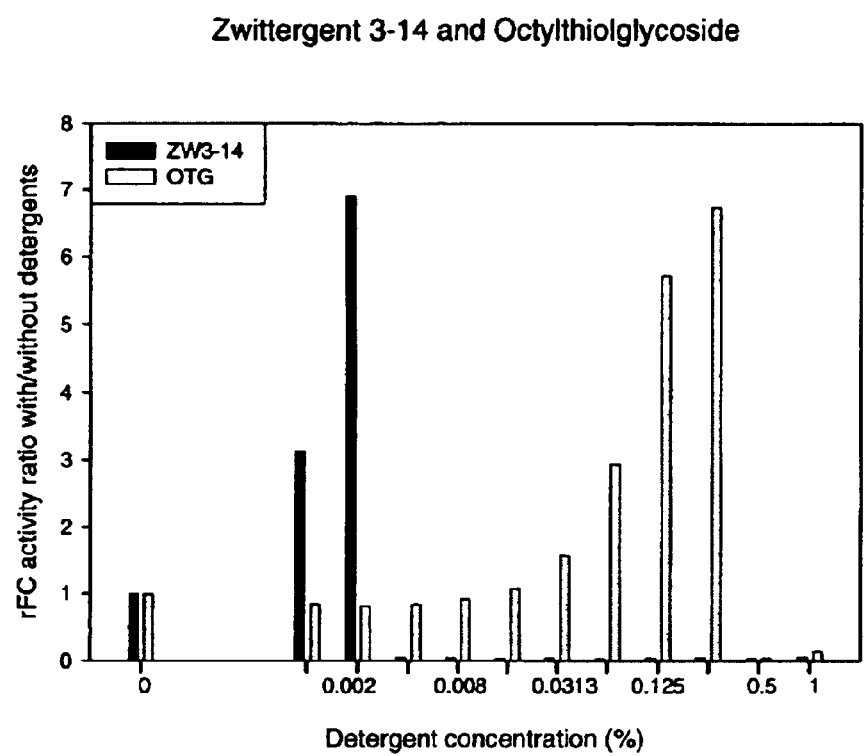
FIG. 9. Graph showing effect of Zwittergent 3-14 and octylthiolglycoside on recombinant Factor C activity.
Figure 10:
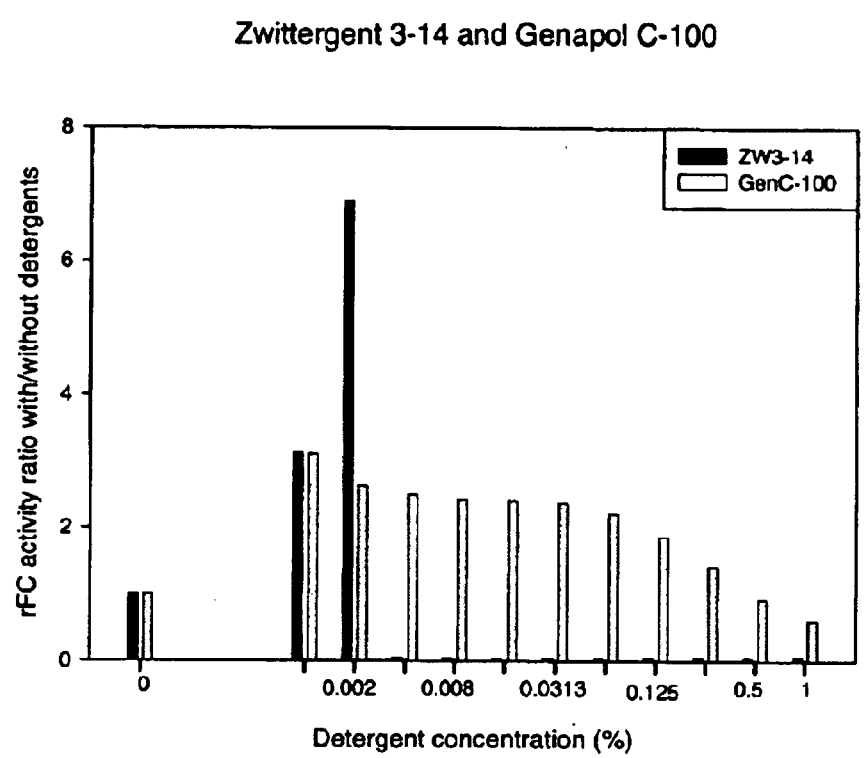
FIG. 10. Graph showing effect of Zwittergent 3-14 and Genapol C-100 on recombinant Factor C activity.
Figure 11:
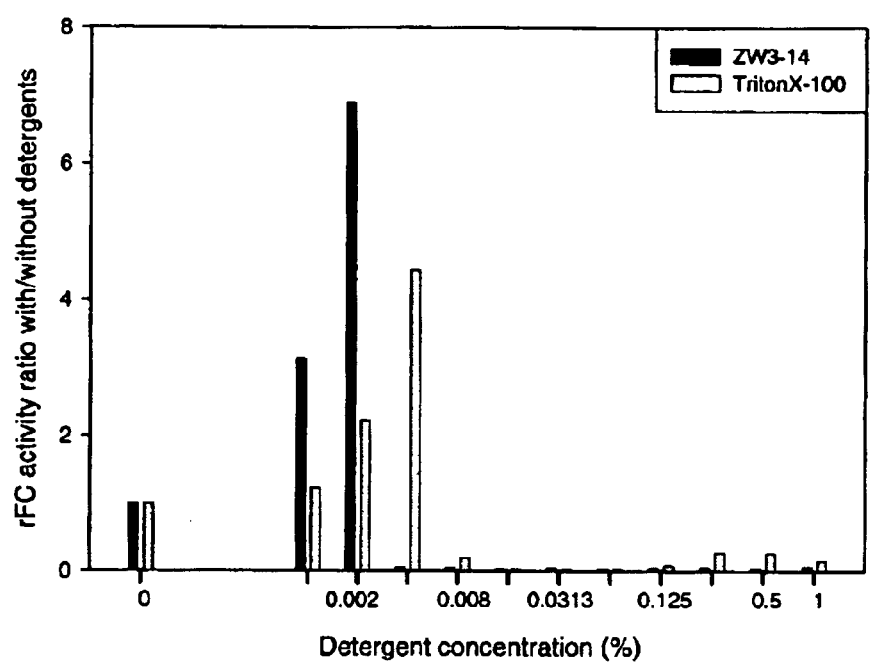
FIG. 11. Graph showing effect of Zwittergent 3-14 and TX-100 on recombinant Factor C activity.

The results of a one-step recombinant Factor C endotoxin assay are shown in FIG. 8.

---

What is claimed is:

1. A reagent for increasing sensitivity of enzymatic endotoxin detection, comprising:
   a purified horseshoe crab Factor C protein; and
   a surfactant,
   wherein the purified horseshoe crab Factor C protein is enzymatically active in the presence of the surfactant and wherein the surfactant is present in an amount which increases the sensitivity of an enzymatic endotoxin detection reaction relative to a reagent containing the purified horseshoe crab Factor C protein but which does not comprise the surfactant.

2. The reagent of claim 1 wherein the surfactant is selected from the group consisting of:
   I amphoteric surfactants represented by the following formulae

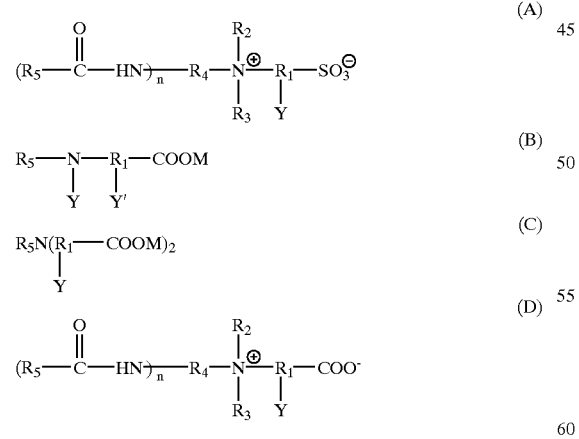

wherein $R_1$ is an alkylene radical having from 1 to 4 carbon atoms;
Y and Y' are each hydrogen or a substituted or unsubstituted lower alkyl;
$R_2$ and $R_3$ are each a substituted or unsubstituted lower alkyl;
n is 0 or 1, wherein when n is 0, $R_4$ is alkyl containing from about 8 to about 18 carbon atoms,
and when n is 1, $R_4$ is an alkcylene radical having from 1 to about 6 carbon atoms;
$R_5$ is a substituted or unsubstituted alkyl; and
M is hydrogen or a salt-forming metal;
(II) anionic surfactants represented by the following formulae:

$$(R_6)_{n1}\text{-}(Y)Ar(SO_3M)_{n2} \qquad (E)$$

wherein $R_6$ is a straight or branched chain hydrocarbon radical having from about 1 to about 24 carbon atoms, wherein at least one $R_6$ has at least 8 carbon atoms;
n1 is from 1 to 3;
n2 is from 1 to 2;
Ar is a phenyl or a naphthyl radical; and
Y and M have the same meaning as in Formula (B);

$$R_5OSO_3M \qquad (F)$$

wherein M has the same meaning as in Formula (B);
(III) cationic surfactants represented by the following formula:

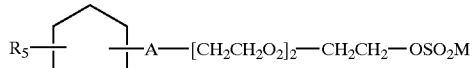

wherein
A is either oxygen, sulfur, a carbonamide group, a thiocarbonamide group, a carboxylic group, or a thiocarboxylic ester group;
z is an integer from 3 to 8; and M has the same meaning as in Formula (B);

(IV) nonionic surfactants represented by the following formula:

$$R_5R_7R_8N \rightarrow O \quad (H)$$

wherein $R_5$ has the same meaning as in Formula (A);

$R_7$ and $R_8$ are each methyl or ethyl;

(IV) cationic surfactants represented by the following formulae:

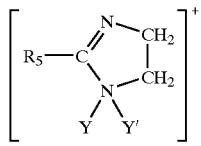

(I)

wherein $R_5$, Y, and Y' have the same meaning as in Formula C;

$$R_9NHO_2H_4NH_2 \quad (J)$$

wherein R is an alkyl group of about 12 to 22 carbon atoms;

$$R_5CONHC_2H_4NH_3 \quad (K)$$

wherein $R_5$ has the same meaning as in Formula (A);

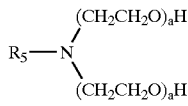

(L)

wherein $R_5$ has the same meaning as in Formula A and each a is an integer from 1 to 15; and (V) those nonionic surfactants selected from the group consisting of the condensation product of about 10 to 30 moles of ethylene oxide with the monoester of a hexahydric alcohol containing 6 carbon atoms with the ester group containing 10 to 20 carbon atoms.

3. The reagent of claim 1 wherein the horseshoe crab is *Limulus polyphemus*.

4. The reagent of claim 1 wherein the horseshoe crab is *Carcinoscorpius rotundicauda*.

5. The reagent of claim 1 wherein the horseshoe crab is *Tachypleus tridentatus*.

6. The reagent of claim 1 wherein the horseshoe crab is *Tachypleus gigas*.

7. The reagent of claim 1 wherein the Factor C protein is made by the method of culturing a host cell comprising a vector encoding the Factor C protein in a supernatant under conditions such that the Factor C protein is expressed into the supernatant.

8. The reagent of claim 7 wherein the host cell is an Sf9 cell.

9. The reagent of claim 7 wherein the horseshoe crab is *Carcinoscorpius rotundicauda*.

10. The reagent of any one of claims 1 through 9 wherein the surfactant is selected from the group consisting of ZWITTERGENT 3-14, Triton X-100, Triton X-114, octyl-beta-D-thioglucoside, Genapol C-100, Tween 20, and Tween 80.

11. A method of detecting endotoxin in a test sample, comprising the steps of:

contacting a test sample with (1) the reagent of claim 1 and (2) a Factor C substrate to form a test sample-substrate-reagent mixture, wherein cleavage of the Factor C substrate generates a detectable signal; and assaying the test sample-substrate-reagent mixture for the presence or absence of the detectable signal, wherein an amount of the detectable signal that is increased relative to a control sample that does not contain endotoxin indicates a presence of endotoxin in the test sample.

12. The method of claim 11 wherein the horseshoe crab is *Limulus polyphemus*.

13. The method of claim 11 wherein the horseshoe crab is *Carcinoscorpius rotundicauda*.

14. The method of claim 11 wherein the horseshoe crab is *Tachypleus tridentatus*.

15. The method of claim 11 wherein the horseshoe crab is *Tachypleus gigas*.

16. The method of claim 11 wherein the Factor C protein is made by the method of:

culturing a host cell comprising a vector encoding the Factor C protein in a supernatant under conditions such that the Factor C protein is expressed into the supenatant.

17. The method of claim 16 wherein the host cell is an Sf9 cell.

18. The method of claim 15 wherein the horseshoe crab is *Carcinoscorpius rotundicauda*.

19. The method of any one of claims 10–18 wherein the surfactant is selected from the group consisting of ZWITTERGENT 3-14, Triton X-100, Triton X-114, octyl-beta-D-thioglucoside, Genapol C-100, Tween 20, and Tween 80.

20. The method of claim 11 wherein the Factor C substrate is selected from the group consisting of N-t-BOC-Asp(Obzl)-Pro-Arg-7-Amido-4-methyl coumarin and N-t-BOC-Val-Pro-Arg-7-Amido-4-methyl coumarin.

21. A method of detecting endotoxin in a test sample, comprising the steps of:

contacting a test sample with:

(1) a reagent comprising (a) a surfactant in an amount which increases the sensitivity of an enzymatic endotoxin detection reaction relative to a reagent containing a purified horseshoe crab Factor C protein but which does not comprise the surfactant and (b) a recombinant *Carcinoscorpius rotundicauda* Factor C protein, wherein the Factor C protein is made by the method of culturing a host cell comprising a vector encoding the Factor C protein in a supernatant under conditions such that the Factor C protein is expressed into the supernatant, wherein the Factor C protein is enzymatically active in the presence of the surfactant; and (2) N-t-BOC-Asp(Obzl)-Pro-Arg-7-Amido-4-methyl coumarin to form a test sample-substrate-reagent mixture; and assaying the test sample-substrate-reagent mixture for the presence or absence of a fluorescent signal, wherein an amount of the fluorescent signal that is increased relative to a control sample that does not contain endotoxin indicates a presence of endotoxin in the test sample.

22. The method of claim 21 wherein the host cell is an Sf9 cell.

23. A kit for detecting endotoxin, comprising:

the reagent of claim 1; and instructions for the method of claim 11.

24. The kit of claim 23 further comprising a Factor C substrate, wherein cleavage of the Factor C substrate generates a detectable signal.

25. The kit of claim 24 wherein the Factor C substrate is selected from the group consisting of N-t-BOC-Asp(Obzl)-Pro-Arg-7-Amido-4-methyl coumarin and N-t-BOC-Val-Pro-Arg-7-Amido-4-methyl coumarin.

26. The kit of claim 23 wherein the purified Factor C is made by the method of culturing a host cell comprising a vector encoding the Factor C protein in a supernatant under conditions such that the Factor C protein is expressed into the supernatant.

27. The kit of claim 26 wherein the host cell is an Sf9 cell.

28. A method of detecting endotoxin in a test sample, comprising the steps of:

contacting a test sample with the reagent of claim 1 to form a test sample-reagent mixture;

contacting the test sample-reagent mixture with a Factor C substrate, wherein cleavage of the Factor C substrate generates a detectable signal to form a test sample-substrate-reagent mixture; and assaying the test sample-substrate-reagent mixture for the presence or absence of the detectable signal, wherein an amount of the detectable signal that is increased relative to a control sample that does not contain endotoxin indicates a presence of endotoxin in the test sample.

29. A method of detecting endotoxin in a test sample, comprising the steps of:

contacting a test sample with a reagent comprising (a) a surfactant in an amount which increases sensitivity of an enzymatic endotoxin reaction relative to a reagent containing a purified horseshoe crab Factor C protein but which does not comprise the surfactant, and (b) a recombinant *Carcinoscorpius rotundicauda* Factor C protein, wherein the Factor C protein is made by the method of culturing a host cell comprising a vector encoding the Factor C protein in a supernatant under conditions such that the Factor C protein is expressed into the supernatant, wherein the Factor C protein is enzymatically active in the presence of the surfactant to form a test sample-reagent mixture;

contacting the test sample-reagent mixture with N-t-BOC-Asp(Obzl)-Pro-Arg-7-Amido-4-methyl coumarin to form a test substance-substrate-reagent mixture; and assaying the test sample-substrate-reagent mixture for the presence or absence of a fluorescent signal, wherein an amount of the fluorescent signal that is increased relative to a control sample that does not contain endotoxin indicates a presence of endotoxin in the test sample.

30. A reagent for increasing sensitivity of enzymatic endotoxin detection comprising:

a purified recombinant *Carcinoscorpius rotundicauda* Factor C protein; and ZWITTERGENT 3-14, wherein the *Carcinoscorpius rotundicauda* Factor C protein is enzymatically active in the presence of the ZWITTERGENT 3-14 and wherein the ZWITTERGENT 3-14 is present in an amount that increases the sensitivity of an enzymatic detection reaction relative to a reagent that comprises the purified recombinant *Carcinoscorpius rotundicauda* Factor C protein but does not comprise the ZWITTERGENT 3-14.

31. The reagent of claim 30 further comprising a Factor C substrate.

32. The reagent of claim 31 wherein the Factor C substrate is N-t-BOC-Asp(Obzl)-Pro-Arg-7-Amido-4-methyl coumarin.

33. The reagent of any one of claims 1 through 9 wherein the surfactant is ZWITTERGENT 3-14.

34. The reagent of claim 1 further comprising a Factor C substrate.

35. The reagent of claim 34 wherein the Factor C substrate is N-t-BOC-Asp(Obzl)-Pro-Arg-7-Amido-4-methyl coumarin.

36. A method of detecting endotoxin in a test sample, comprising the steps of:

contacting a test sample with the reagent of claim 30 to form a test sample-reagent mixture;

contacting the test sample-reagent mixture with a Factor C substrate, wherein cleavage of the Factor C substrate generates a detectable signal, to form a test sample-substrate-reagent mixture; and assaying the test sample-substrate-reagent mixture for the presence or absence of the detectable signal, wherein an amount of the detectable signal that is increased relative to a control sample that does not contain endotoxin indicates a presence of endotoxin in the test sample.

37. A method of detecting endotoxin in a test sample, comprising the steps of:

contacting a test sample with (1) the reagent of claim 30 and (2) N-t-BOC-Asp(Obzl)-Pro-Arg-7-Amido-4-methyl coumarin to form a test sample-substrate-reagent mixture; and assaying the test sample-substrate-reagent mixture for the presence or absence of a fluorescent signal, wherein an amount of the fluorescent signal that is increased relative to a control sample that does not contain endotoxin indicates a presence of endotoxin in the test sample.

38. A kit comprising:

the reagent of claim 30; and instructions for the method of claim 37.

39. The kit of claim 38, further comprising a Factor C substrate.

40. The kit of claim 39 wherein the Factor C substrate is N-t-BOC-Asp(Obzl)-Pro-Arg-7-Amido-4-methyl coumarin.

41. A reagent for increasing sensitivity of enzymatic endotoxin detection, comprising:

0.03–3 µg/ml of a purified horseshoe crab Factor C protein; and a surfactant, wherein the purified horseshoe crab Factor C protein is enzymatically active in the presence of the surfactant and wherein the surfactant is present in an amount which increases the sensitivity of an enzymatic endotoxin detection reaction relative to a reagent containing the purified horseshoe crab Factor C protein but which does not comprise the surfactant.

42. A reagent for increasing sensitivity at enzymatic endotoxin detection, comprising:

a purified horseshoe crab Factor C protein; and 0.001–0.003% of a surfactant, wherein the purified horseshoe crab Factor C protein is enzymatically active in the presence of the surfactant and wherein the surfactant is present in an amount which increases the sensitivity of an enzymatic endotoxin detection reaction relative to a reagent containing the purified horseshoe crab Factor C protein but which does not comprise the surfactant.

43. A reagent for increasing sensitivity of enzymatic endotoxin detection, comprising:

0.03–3 µg/ml of a purified recombinant *Carcinoscorpius rotundicauda* Factor C protein; and

ZWITTERGENT 3-14, wherein the *Carcinoscorpius rotundicauda* Factor C protein is enzymatically active in the presence of the ZWITTER- GENT 3-14 and wherein the ZWITTERGENT 3-14 is present in an amount that increases the sensitivity of an enzymatic detection reaction relative to a reagent that comprises the purified recombinant *Carcinoscorpius rotundicauda* Factor C protein but does not comprise the ZWITTERGENT 3-14.

44. A reagent for increasing sensitivity of enzymatic endotoxin detection, comprising:
  a purified recombinant *Carcinoscorpius rotundicauda* Factor C protein; and
  0.0025% of ZWITTERGENT 3-14, wherein the *Carcinoscorpius rotundicauda* Factor C protein is enzymatically active in the presence of the ZWITTERGENT 3-14 and wherein the ZWITTERGENT 3-14 is present in an amount that increases the sensitivity of an enzymatic detection reaction relative to a reagent that comprises the purified recombinant *Carcinoscorpius rotundicauda* Factor C protein but does not comprise the ZWITTERGENT 3-14.

* * * * *

UNITED STATES PATENT AND TRADEMARK OFFICE
CERTIFICATE OF CORRECTION

PATENT NO. : 6,849,426 B2  Page 1 of 1
DATED : February 1, 2005
INVENTOR(S) : Lin Chen et al.

It is certified that error appears in the above-identified patent and that said Letters Patent is hereby corrected as shown below:

Column 47,
Line 42, please delete "I" with -- (I) --.

Column 48,
Line 30, please replace "alkcylene" with -- alkylene --.

Column 49,
Line 24, please replace "$R_9NHO_2H_4NH_2$" with -- $R_9NHC_2H_4NH_2$ --.

Signed and Sealed this

First Day of November, 2005

JON W. DUDAS
*Director of the United States Patent and Trademark Office*